US012796754B2

(12) United States Patent
Jayaraman et al.

(10) Patent No.: US 12,796,754 B2
(45) Date of Patent: Nov. 17, 2026

(54) RESPIRATORY PROTECTIVE DEVICE WITH ATTACHMENT SUPPORT MEMBER

(71) Applicant: Georgia Tech Research Corporation, Atlanta, GA (US)

(72) Inventors: Sundaresan Jayaraman, Atlanta, GA (US); Sungmee Park, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 764 days.

(21) Appl. No.: 18/162,323

(22) Filed: Jan. 31, 2023

(65) Prior Publication Data

US 2023/0240390 A1 Aug. 3, 2023

Related U.S. Application Data

(60) Provisional application No. 63/304,893, filed on Jan. 31, 2022.

(51) Int. Cl.
*A41D 13/11* (2006.01)
*A62B 18/02* (2006.01)
(Continued)

(52) U.S. Cl.
CPC ...... *A41D 13/1161* (2013.01); *A41D 13/1107* (2013.01); *A41D 13/1153* (2013.01);
(Continued)

(58) Field of Classification Search
CPC ............ A41D 13/1161; A41D 13/1107; A41D 13/1153; A41D 13/11; A41D 2200/20; A62B 18/02; A62B 18/08; A62B 18/025; A62B 18/084; A62B 27/00; A62B 17/04; A61M 2207/10; A61M 16/0683;
(Continued)

(56) References Cited

U.S. PATENT DOCUMENTS 1,942,442 A * 1/1934 Motsinger ............ A62B 18/084 2/9
2,176,709 A * 10/1939 Dym .................... A62B 18/084 24/116 R
(Continued)

OTHER PUBLICATIONS

"3dMD Products", Retrieved from https://3dmd.com/products/, 5 pages, Oct. 15, 2024.
(Continued)

*Primary Examiner* — Rachel T Sippel
*Assistant Examiner* — Gwynneth L Howell
(74) *Attorney, Agent, or Firm* — Meunier Carlin & Curfman LLC

(57) ABSTRACT

An exemplary respiratory-protective-device attachment supporting apparatus (also referred to as a hub or fastening hub) and method are disclosed that can be placed at the parietal region of a person's head and connected to the respiratory protective device via one or more straps. The attachment supporting apparatus provides a large surface area for the securing of the respiratory protective device to the face to enhance the fit and comfort of the respiratory protective device. The attachment supporting apparatus also facilitates the correct, rapid, and repeatable donning of the RPD to ensure the proper protection against inhalation hazards.

20 Claims, 15 Drawing Sheets

*FIG. 1*

(51) Int. Cl.
*A62B 18/08* (2006.01)
*A62B 27/00* (2006.01)

(52) U.S. Cl.
CPC .............. *A62B 18/02* (2013.01); *A62B 18/08* (2013.01); *A62B 27/00* (2013.01); *A61M 2207/10* (2013.01)

(58) Field of Classification Search
CPC .. A42B 1/041; A42B 1/24; A42B 1/00; A42B 1/014; A42B 1/04; A42B 1/048; A42B 1/049
See application file for complete search history.

(56) References Cited

U.S. PATENT DOCUMENTS

| | | | | | |
|---|---|---|---|---|---|
| 3,013,556 | A * | 12/1961 | Galleher, Jr. | A62B 18/084 2/206 |
| 3,040,741 | A | 6/1962 | Carolan | |
| 6,701,925 | B1 | 3/2004 | Resnick | |
| 8,573,199 | B2 | 11/2013 | King et al. | |
| 10,646,731 | B2 | 5/2020 | Jayaraman et al. | |
| 10,646,732 | B2 | 5/2020 | Rachapudi et al. | |
| 10,843,015 | B2 | 11/2020 | Patil et al. | |
| 11,484,734 | B2 * | 11/2022 | Waterford | B33Y 80/00 |
| 11,969,035 | B2 * | 4/2024 | Qu | A62B 18/084 |
| 2011/0197341 | A1 * | 8/2011 | Formica | B32B 5/024 2/209.3 |
| 2012/0042878 | A1 | 2/2012 | Woo | |
| 2015/0040910 | A1 | 2/2015 | Koehler | |
| 2015/0157822 | A1 * | 6/2015 | Karpas | G06V 40/193 700/98 |
| 2016/0354571 | A1 * | 12/2016 | Grashow | A61M 16/065 |
| 2017/0173371 | A1 | 6/2017 | Truex et al. | |
| 2017/0361045 | A1 | 12/2017 | Fu et al. | |
| 2019/0134436 | A1 * | 5/2019 | Thompson | A62B 18/084 |
| 2020/0114178 | A1 | 4/2020 | Waterford et al. | |
| 2021/0322796 | A1 * | 10/2021 | Hubbard | B01D 39/083 |
| 2021/0361003 | A1 | 11/2021 | Barr | |
| 2021/0402222 | A1 | 12/2021 | Kwon et al. | |
| 2022/0024139 | A1 | 1/2022 | Schwartz et al. | |
| 2022/0105369 | A1 * | 4/2022 | Lee | A41D 13/1161 |
| 2023/0047226 | A1 * | 2/2023 | van Zanten | A61M 16/024 |
| 2023/0149647 | A1 | 5/2023 | Evans et al. | |
| 2023/0284714 | A1 | 9/2023 | Chahine et al. | |

OTHER PUBLICATIONS

"Carbon Inc.-SIL 30", DOI—<<https://www.carbon3d.com/materials/sil-30>>, 8 pages, Oct. 15, 2024.
"Chart from CES EduPack", ANSYS Granta, Oct. 15, 2024.
"Elastic 50A", Formlabs, Soft Flexible Prototypes, DOI:—<<https://formlabs.com/materials/flexible-elastic/>>, 6 pages, Jun. 19, 2022.
"Preparing for an Influenza Pandemic: Personal Protective Equipment for Healthcare Workers", Institute of Medicine, 11 pages, Oct. 15, 2024.
"Protecting Facial Skin Under N95 Face Masks", National Pressure Injury Advisor Panel, DOI:—<<https://cdn.ymaws. com/npiap.com/resource/resmgr/position_statements/NPIAP_-_Mask_Injury_Infograp.pdf>>, 1 page, 2020.
"Reusability of Facemasks During an Influenza Pandemic: Facing the Flu", Institute of Medicine, 10 pages, Oct. 15, 2024.
"Reusable Elastomeric Respirators in Health Care: Considerations for Routine and Surge Use", National Academies of Sciences, Engineering, and Medicine, 10 pages, Oct. 15, 2024.
"Silastic™M 3D 3335 Liquid Silicone Rubber", Dow, DOI:—<<https://www.dow.com/en-us/pdp.silastic-3-d-3335-liquid-silicone-rubber-Isr.4137603z.html?productCatalogFlag=1#overview>., 2 pages, 2022.
"Silicones 3D Flyer Industrial", Elkem, Available on: <<https://www.elkem.com/silicones/brands/amsil/>>,3 pages, Oct. 15, 2024.
Ashby, M F, "The CES EduPack Database of Natural and Man-Made Materials", Version 1.0, Granta Design, Jan. 2008.
Cai, et al., "Customized Design and 3D Printing of Face Seal for an N95 Filtering Facepiece Respirator", Journal of Occupational and Environmental Hygiene, vol. 15, No. 3, pp. 226-234, Mar. 2018.
Chopra, et al., "The Influence of Gender and Ethnicity on Facemasks and Respiratory Protective Equipment Fit: A Systematic Review and Meta-analysis", BMJ Global Health, vol. 6, No. 11, Article No. e005537, pp. 1-18, Nov. 2021.
D'Agostino, Susan, "Voronoi Tessellations and Scutoids Are Everywhere", Scientific American, DOI:—<<https://blogs.scientificamerican.com/observations/voronoi-tessellations-and-scutoids-are-everywhere/>>, 7 pages, Jan. 22, 2019.
Lam, et al., "N95 Respirator Associated Pressure Ulcer Amongst COVID-19 Health Care Workers", International Wound Journal, vol. 17, No. 5, pp. 1525-1527, Oct. 2020.
Lee, et al., "A 3D Anthropometric Sizing Analysis System Based on North American Caesar 3D Scan Data for Design of Head Wearable Products", Computers & Industrial Engineering, vol. 117, pp. 121-130, Mar. 2018.
Lin, et al., "Characterization of Small-to-medium Head-and-face Dimensions for Developing Respirator Fit Test Panels and Evaluating Fit of Filtering Facepiece Respirators With Different Faceseal Design", PLoS One, vol. 12, No. 11, Article No. e0188638, pp. 1-26, Nov. 27, 2017.
Oot-Giromini, et al., "Pressure Ulcer Prevention Versus Treatment, Comparative Product Cost Study", Decubitus, vol. 2, No. 3, Aug. 1989, pp. 52-54.
Roberge, et al., "Analysis of Forces Generated by N95 Filtering Facepiece Respirator Tethering Devices: A Pilot Study", Journal of Occupational and Environmental Hygiene, vol. 9, No. 8, pp. 527-533, 2012.
Shore, "Durometer Shore Hardness Scale", DOI:—https://www.smooth-on.com/page/durometer-shore-hardness- scale/, 2 pages, 2020.
Stokowski, Laura A., "A Step-by-Step Guide to Preventing PPE-Related Skin Damage", Retrieved from: <<https://www.medscape.com/viewarticle/929590>>, 9 pages, Apr. 28, 2020.
Yang, et al., "Simulating the Interaction between a Respirator and a Headform Using LS-DYNA", Computer-Aided Design and Applications, vol. 6, No. 4, pp. 539-551, 2009.
Zhuang, et al., "Correlation Between Respirator Fit and Respirator Fit Test Panel Cells by Respirator Size", Journal of Occupational and Environmental Hygiene, vol. 5, No. 10, pp. 617-628, Oct. 2008.
Zhuang, et al., "Head-and-Face Anthropometric Survey of U.S. Respirator Users", Journal of Occupational and Environmental Hygiene, vol. 2, No. 11, pp. 567-576, Nov. 2005.
Zhuang, et al., "Recommended Test Methods and Pass/Fail Criteria for a Respirator Fit Capability Test of Half-mask Air-purifying Respirators", Journal of Occupational and Environmental Hygiene, vol. 14, No. 6, pp. 473-481, Jun. 2017.
3M: "Cleaning and Disinfecting 3M Reusable Elastomeric Half and Full Facepiece Respirators following Potential Exposure to Coronaviruses," 3M Personal Safety Division, Aug. 2022, pp. 1-7, Retrieved from URL: https://multimedia.3m.com/mws/media/17939590/cleaning-and-disinfecting-3m-reusable-respirators-following-potential- exposure-to-coronaviruses.pdf.
Cai M., et al., "Customized Design and 3D Printing of Face Seal for an N95 Filtering Facepiece Respirator," Journal of Occupational and Environmental Hygiene, 2018, vol. 15, No. 3, pp. 226-234 (26 Pages) Retrieved from URL: https://doi.org/10.1080/15459624.2017.1411598.
Contrera J., "The N95 Shortage America Can't Seem to Fix," The Washington Post, Sep. 21, 2020, pp. 1-55.
DOW: "Silastic 3D 3335 Liquid Silicone Rubber," 2022, 2 Pages, [Retrieved on Jun. 18, 2022] Retrieved from URL: https://www.dow.com/en-us/pdp.silastic-3-d-3335-liquid-silicone-rubber- Isr.4137603z.htmlproductCatalogFlag=I#overview.
Final Office Action for U.S. Appl. No. 18/162,315 dated Aug. 25, 2025, 18 pages.
Goldfrank L.R., et al., (Eds)., "Preparing for an Influenza Pandemic: Personal Protective Equipment for Healthcare Workers," Institute of Medicine of the National Academies, Washington, DC, 2008, 207 Pages. Retrieved from URL: https://doi.org/10.17226/11980.

(56) References Cited

OTHER PUBLICATIONS

Lam S.C., et al., "Sensitivity and Specificity of the User-Seal-Check in Determining the Fit of N95 Respirators," Journal of Hospital Infection, 2011, vol. 77, pp. 252-256, Retrieved from URL: https://doi.Org/10.1016/j.jhin.2010.09.034.
National Academies of Sciences, Engineering, and Medicine: "Frameworks for Protecting Workers and the Public from Inhalation Hazards," Washington, DC, The National Academies Press, US, Feb. 10, 2022, pp. 1-2, Retrieved from URL: https://doi.org/10.17226/26372.
Notice of Allowance for U.S. Appl. No. 18/162,312, mailed Oct. 28, 2025, 8 pages.
Radonovich Jr.L.J., et al., "Respirator Tolerance in Health Care Workers," Journal of the American Medical Association, Jan. 7, 2009, vol. 301, No. 1, pp. 36-38, DOI: 10.1001/jama.2008.894.
The National Academies Press: "Reusable Elastomeric Respirators in Health Care: Considerations for Routine and Surge Use," National Academies of Sciences, Engineering, and Medicine, Washington, DC, 2019, pp. 1-33, Retrieved from URL: https://doi.org/10.17226/25275, https://nap.nationalacademies.Org/read/25275/chapter/l.
Zhuang Z., et al., "Correlation Between Respirator Fit and Respirator Fit Test Panel Cells by Respirator Size," Journal of Occupational and Environmental Hygiene, 2008, vol. 5, No. 10, pp. 617-628 (3 Pages), Retrieved from URL: https://doi.org/10.1080/15459620802293810.
Zhuang Z., et al., "Head-and-Face Anthropometric Survey of U.S. Respirator Users," Journal of Occupational and Environmental Hygiene, PMID: 16223715, Nov. 2005, vol. 2, No. 11, pp. 567-576 (1 Page), Retrieved from URL: https://10.1080/15459620500324727.
Zhuang Z., et al., "Recommended Test Methods and Pass/Fail Criteria for a Respirator Fit Capability Test of Half-Mask Air-Purifying Respirators," Journal of Occupational and Environmental Hygiene, 2017, vol. 14, No. 6, pp. 473-481 (4 Pages) Retrieved from URL: https://doi.org/10.1080/15459624.2017.1296233.
Niosh, https://www.cdc.gov/niosh/hierarchy-of-controls/about/index.html.
Park, S., Tian, Y., Bergman, M., Pollard, J., Zhuang, Z., and Jayaraman, S., Next Generation Custom-Fit Reusable Respiratory Protective Device with Continuous Fit Monitoring—Part I: Custom-Fit Design, Journal of the International Society of Respiratory Protection, vol. 41, No. 1, 2024, 22-37.
Roberge R, Niezgoda G, and Benson S. (2012) Analysis of Forces Generated by N95 Filtering Facepiece Respirator Tethering Devices: A Pilot Study, Journal of Occupational and Environmental Hygiene, 9 (8), 527-533.
Yang J, Dai J, Zhuang Z. (2009) Simulating the interaction between a respirator and a headform using LS-DYNA. Computer-Aided Design Appl. 6(4):539-551.
Sungmee Park, et al., Next-Generation Custom-Fit Reusable Respiratory Protective Device with Continuous Fit Monitoring—Part III: 3D Printing of Prototypes and Evaluation. Journal of the International Society for Respiratory Protection, vol. 41, No. 2, 2024, 12 pages.
OSHA 1910.134 App A, Fit Testing Procedures (Mandatory), https://www.osha.gov/laws regs/regulations/standardnumber/1910/1910.134AppA.
Stokowski LA. (2020) A Step-by-Step Guide to Preventing PPE-Related Skin Damage. MedScape. Retrieved from https://www.medscape.com/viewarticle/929590.
National Pressure Injury Advisory Panel. (2020) https://cdn.ymaws.com/npiap.com/resource/resmgr/position_statements/NPIAP_-_Mask_Injury_Infograp.pdf.
Jayaraman, S., Next Generation Custom-Fit Reusable N95 Respirator with Fit Monitoring, Final Technical Report, SJ-TR-CDC-06-22. Jun. 30, 2022. 109 pages.
Park, S., Tian, Y., Bergman, M., Pollard, J., Zhuang, Z., and Jayaraman, S., Next Generation Custom-Fit Reusable Respiratory Protective Device with Continuous Fit Monitoring—Part II: Continuous Fit Monitoring, Journal of the International Society of Respiratory Protection, vol. 41, No. 1, Jul. 2024, pp. 38-56.

* cited by examiner

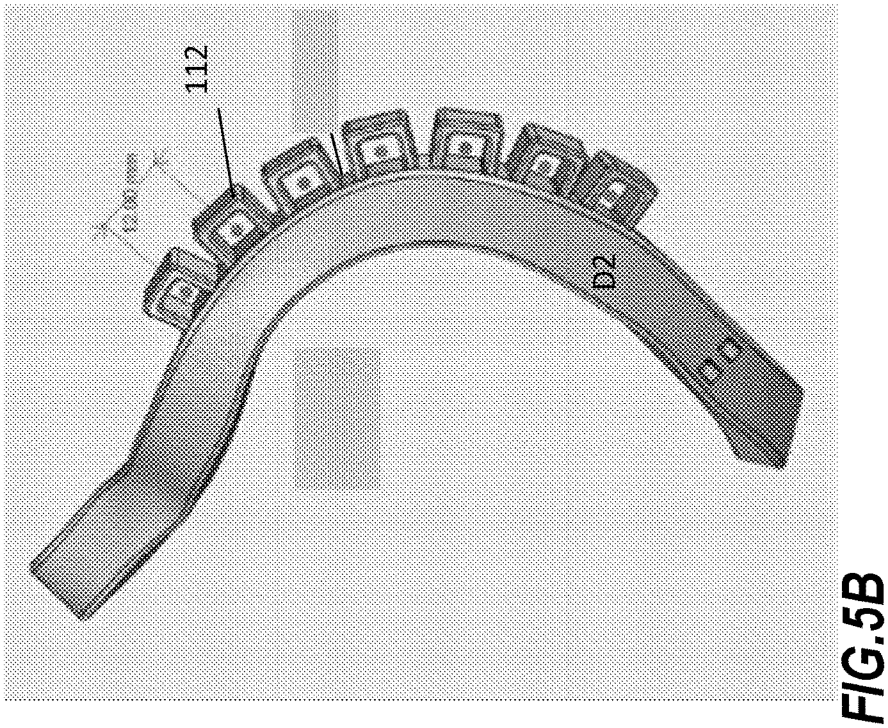
FIG.5B
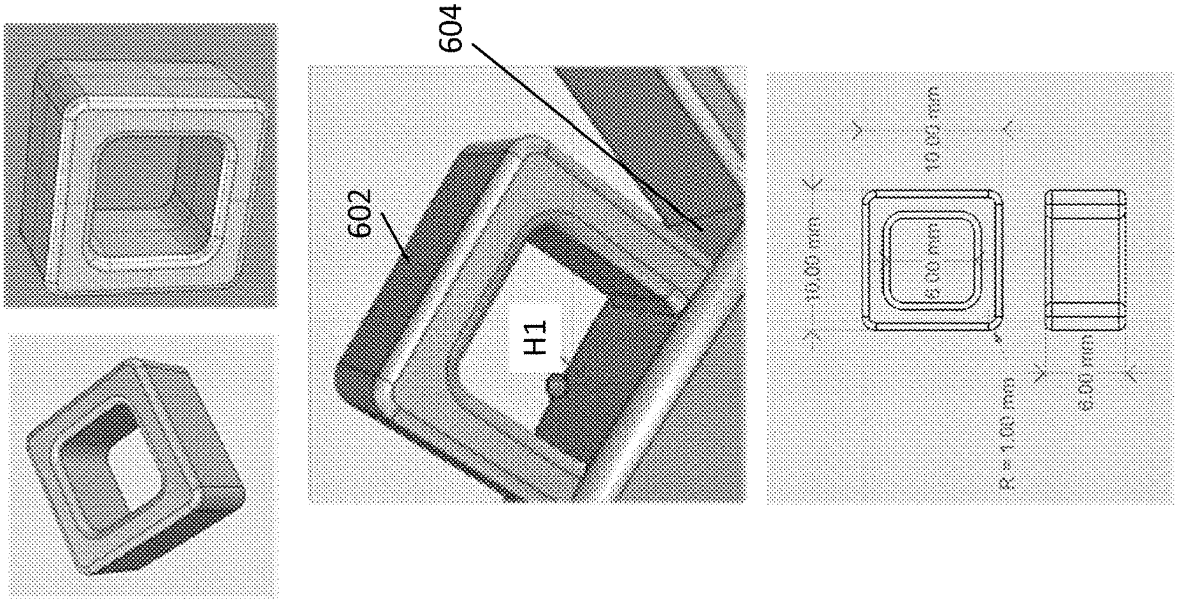

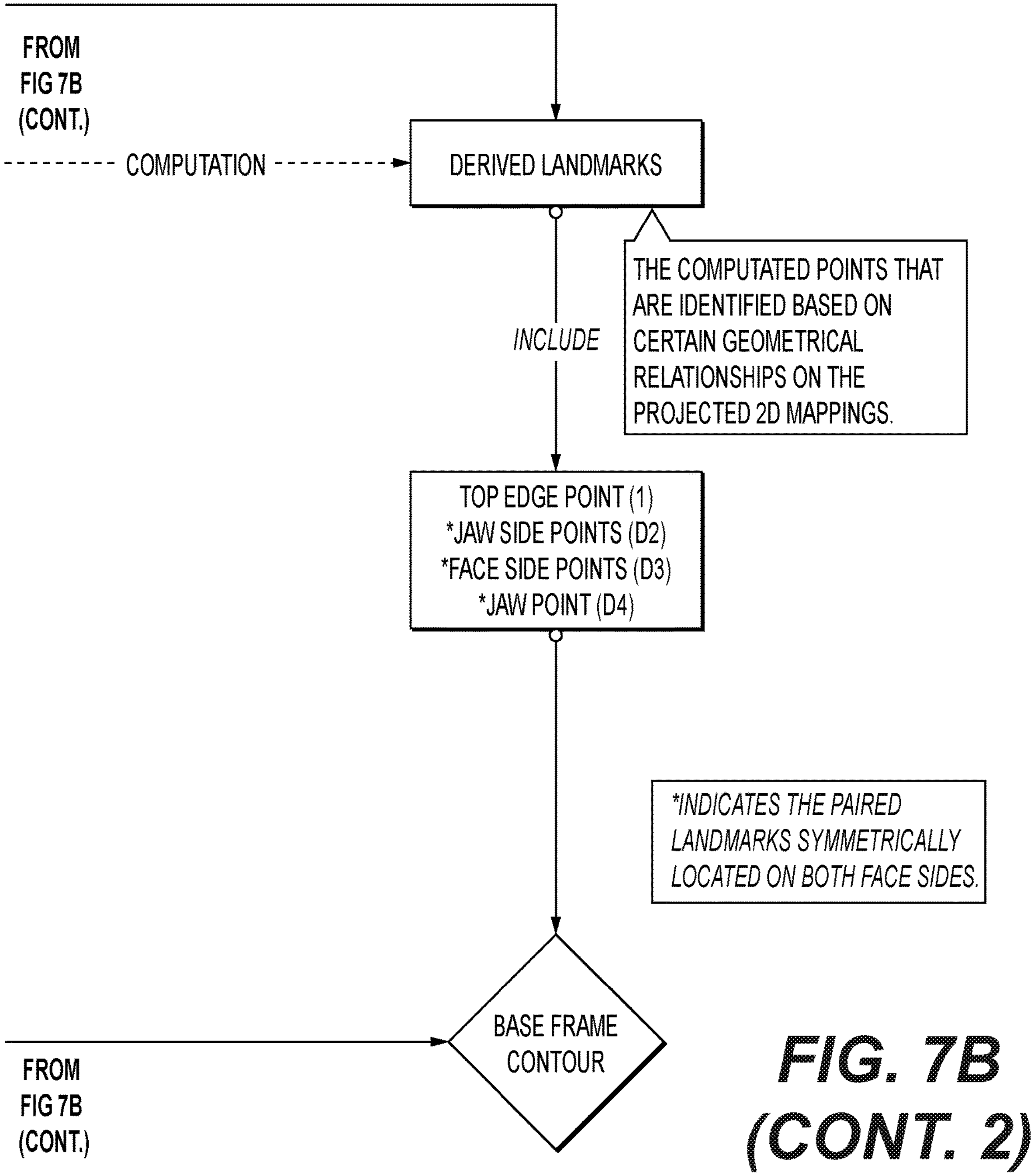
FIG. 7B (CONT. 2)

RESPIRATORY PROTECTIVE DEVICE WITH ATTACHMENT SUPPORT MEMBER

RELATED APPLICATION

This application claims priority to, and the benefit of, U.S. Provisional Patent Application No. 63/304,893, filed Jan. 31, 2022, entitled "RESPIRATOR WITH CONTINUOUS FIT MONITORING," which is incorporated by reference herein in its entirety.

STATEMENT REGARDING FEDERALLY SPONSORED RESEARCH OR DEVELOPMENT

This invention was made with government support under Contract Number: 75D30120C09567 awarded by the Centers for Disease Control and Prevention. The government has certain rights in the invention.

BACKGROUND

Workers and healthcare professionals are required to wear respiratory protective devices (RPD) in various workplaces and medical settings throughout the United States. A respiratory protective device (RPD) protects workers against insufficient oxygen environment, harmful dust, fog, smoke, mist, gas, vapor, spray, and biological hazards or weapons.

Respiratory protective devices protect the user in two basic ways. The first class of devices protects the user by removing contaminants from the air. This first class of devices includes particulate respirators, which filter out airborne particles, and air-purifying respirators with cartridges/canisters, which filter out chemicals, biological material, and gases. The second class of devices protects the user by supplying clean respirable air from another source. This second class of devices includes airline respirators, which use compressed air from a remote source, and self-contained breathing apparatus (SCBA), which include their own air supply.

One type of respiratory protective device includes filtering facepiece respirators (FFRs) which can be configured with a filter, e.g., N95, N99, N100, R95, R99, R100, P95, P99, P100, and HE. The fit of a respiratory protective device, such as an N95 Filtering Face Respirator (FFR), is critical for preventing face seal leakage and effectively protecting the wearer from potential harm or infection from the ambient environment. Two straps are currently used to secure an N95 FFR onto the wearer's face. The pressure exerted by the RPD on the face at the interface affects both the comfort of the wearer and the leakage at the interface, the faceseal.

There is a benefit and/or a need to improve respiratory protective devices and their usage.

SUMMARY

An exemplary respiratory-protective-device attachment supporting apparatus (also referred to as a hub or fastening hub) and method are disclosed that can be placed at the parietal region of a person's head and connected to the respiratory protective device via one or more straps. The attachment supporting apparatus provides a large surface area for the securing of the respiratory protective device (RPD), e.g., facial covering, to the face to enhance the fit and comfort of the respiratory protective device. The attachment supporting apparatus also facilitates the correct, rapid, and repeatable donning of the RPD to ensure the proper protection against inhalation hazards.

The attachment supporting apparatus and the RPD each include one or more anchorable members (e.g., hooks) for placement of one or more straps, preferably two or more, that are adjustable to provide a uniform or pre-defined tension and to maintain the straps' orientation and position over several repeated donning and doffing operations. The apparatus may be customized to a user or group of users such that the fit on a user's head is comfortable and safe.

In some embodiments, the attachment supporting apparatus and/or respiratory-protective device can be customized and/or designed using human anthropometric landmarks. In some embodiments, the attachment supporting apparatus and/or respiratory protective device can be customized for a specific person based on a 3D scan of the person for fabrication using 3D printing technology, e.g., additive manufacturing device using elastomeric materials, e.g., silicone, polyurethane, or rubber. The material can be cleaned/sanitized for repeated use.

In some embodiments, the anchorable members can serve as anchors for attaching adjustable straps with a calibration scale for customizing and controlling the pressure (magnitude and direction) exerted by the RPD on the user's face to account for variability due to different profiles of individuals resulting from different ethnicities, genders, sizes, and age, among others.

The attachment supporting apparatus can serve as a platform for the attachment of other devices including, but not limited to, a flashlight or handheld electric lamp, a microphone, a speaker, and/or a computing or electronic device (e.g., smartphone), e.g., to enable hands-free use.

In an aspect, a respiratory-protective-device attachment supporting apparatus is disclosed, the apparatus comprising: a support member having a contour defining a planar surface having a central hub region to contact and maintain engagement against a parietal region of a person's head, wherein the support member is connected to a respiratory protective device to maintain a pre-defined position of the respiratory protective device over a facial region of the person; and two or more anchorable structures (e.g., hooks, holes, straps) extending from, or formed in, the support member along a portion of the contour, including at the parietal region.

In some implementations, the respiratory protective device (e.g., N95, etc.) is a facial covering (e.g., fabric mask).

In some implementations, the portion of the contour having the two or more anchorable structures includes a circumferential edge along a first side and a second side of the support member.

In some implementations, the support member includes a plurality of gaps (e.g., cell) or is formed of a mesh material to provide a lightweight, breathable surface.

In some implementations, the gaps have a set of pre-defined shapes to define a plurality of struts within a substrate of the support member at the central hub region.

In some implementations, the plurality of struts form a tessellating pattern (e.g., defined by a gap density, number of gaps, proximity of gaps to each other, offset percentages of the gaps, or a combination thereof).

In some implementations, the plurality of gaps is offset from the circumferential edge by a margin.

In some implementations, the apparatus further comprises straps, wherein the straps comprise a marking or calibration scale for customizing and controlling the pressure exerted by the respiratory protective device on the facial region of the person.

In some implementations, the straps extend from or are coupled to two or more anchorable structures.

In some implementations, the contour is over, or in proximity to, at least one of: a vertex region of the head; an occiput region of the head; an inion region of the head; or any region therebetween.

In some implementations, the contour is customized (e.g., modeled, fabricated, designed, or any combination thereof) to a scanned head profile of a person.

In some implementations, the support member is constructed via additive manufacturing or injection molding using elastomeric materials (e.g., silicone, polyurethanes, and/or rubber).

In some implementations, the support member comprises ethyl-vinyl acetate, silicones, polyurethanes, or neoprene.

In some implementations, the support member comprises a material compatible with a decontaminating operation comprising UV radiation or cleaning solvents (e.g., bleach (NaClO, 5%), sanitizer (NH4Cl, 10%), or solvents for elastomeric respirators).

In some implementations, the support member includes a cavity or recess to house electronic components (e.g., for a communication system, modular devices such as lighting, and/or entertainment systems).

In some implementations, the apparatus further comprises an electronic component (e.g., for a communication system, modular devices such as lighting, and/or entertainment system).

In some implementations, the apparatus further comprises an electronics module and an active device (e.g., smartphone, flashlight, microphone, speaker, processor, etc.), each coupled to the support member.

In some implementations, the two or more anchorable structures are holes integral to the support member and extend through the support member from a top side to a bottom side.

In another aspect, a system is disclosed, the system comprising: a respiratory-protective-device attachment supporting apparatus comprising: a support member having a contour defining a planar surface having a central hub region to contact and maintain engagement against a parietal region of a person's head, wherein the support member is connected to a respiratory protective device to maintain a pre-defined position of the respiratory protective device over a facial region of the person; and two or more anchorable structures (e.g., hooks, holes, strap) extending from, or formed in, the support member along a portion of the contour, including at the parietal region; a respiratory protective device having two or more two or more corresponding anchorable structures; (e.g., having a frame defining a face contour that maintains a breathable filter covering over the facial region of a person; and two or more frame hooks disposed on the frame); and two or more straps to connect the respiratory protective device to the attachment supporting apparatus, wherein each of the two or more straps is configurable between at least a first length and a second length (e.g., to adjust pressure at the respiratory protective device at the facial region and the support member at the parietal region).

In another aspect, a method of fabricating a respiratory-protective-device attachment supporting apparatus is disclosed, the method comprising: acquiring (i) a set of images or scans of a person or (ii) a scanned head profile of the person; generating, by a processor, a model that defines a head profile of the person based on (i) the set of images or scans of the person or (ii) the scanned head profile of the person; determining, by the processor, a plurality of anthropometric landmarks, or landmarks derived therefrom, wherein the plurality of anthropometric landmarks, or landmarks derived therefrom, include at least one of a vertex region of the head, an occiput region of the head, an inion region of the head, any region therebetween, or any region proximal thereto; determining, by the processor, using the determined plurality of anthropometric landmarks, or landmarks derived therefrom, at least one of a support member or a contour thereof that can be fit-ably placed on the person that extends over at least one of a vertex region of the head, an occiput region of the head, an inion region of the head, any region therebetween, or any region proximal thereto; wherein the at least one of the support member or the contour thereof is employed in one or more manufacturing operations (additive manufacturing or otherwise, e.g., conventional manufacturing) to manufacture or fabricate the attachment supporting apparatus.

In another aspect, a method is disclosed, the method comprising: providing a respiratory-protective-device attachment supporting apparatus comprising: a support member having a contour defining a planar surface having a central hub region, wherein the support member is connected to a respiratory protective device to maintain a pre-defined position of the respiratory protective device over a facial region of the person; and two or more anchorable structures (e.g., hooks, holes, strap) extending from, or formed in, the support member along a portion of the contour, including at the parietal region; measuring a head region of a user to obtain a plurality of anatomical facial landmarks; and fitting the respiratory-protective-device attachment supporting apparatus or the contour to the head region of the user such that the central hub region contacts and maintains engagement against a parietal region of the person's head.

BRIEF DESCRIPTION OF DRAWINGS

The skilled person in the art will understand that the drawings described below are for illustration purposes only.

FIGS. 5A and 5B each shows an example frame and filter in which the frame includes the anchorable structures to attach to the exemplary attachment supporting apparatus in accordance with an illustrative embodiment.

DETAILED DESCRIPTION

Each and every feature described herein, and each and every combination of two or more of such features, is included within the scope of the present disclosure, provided that the features included in such a combination are not mutually inconsistent.

Example System

Figure 1:
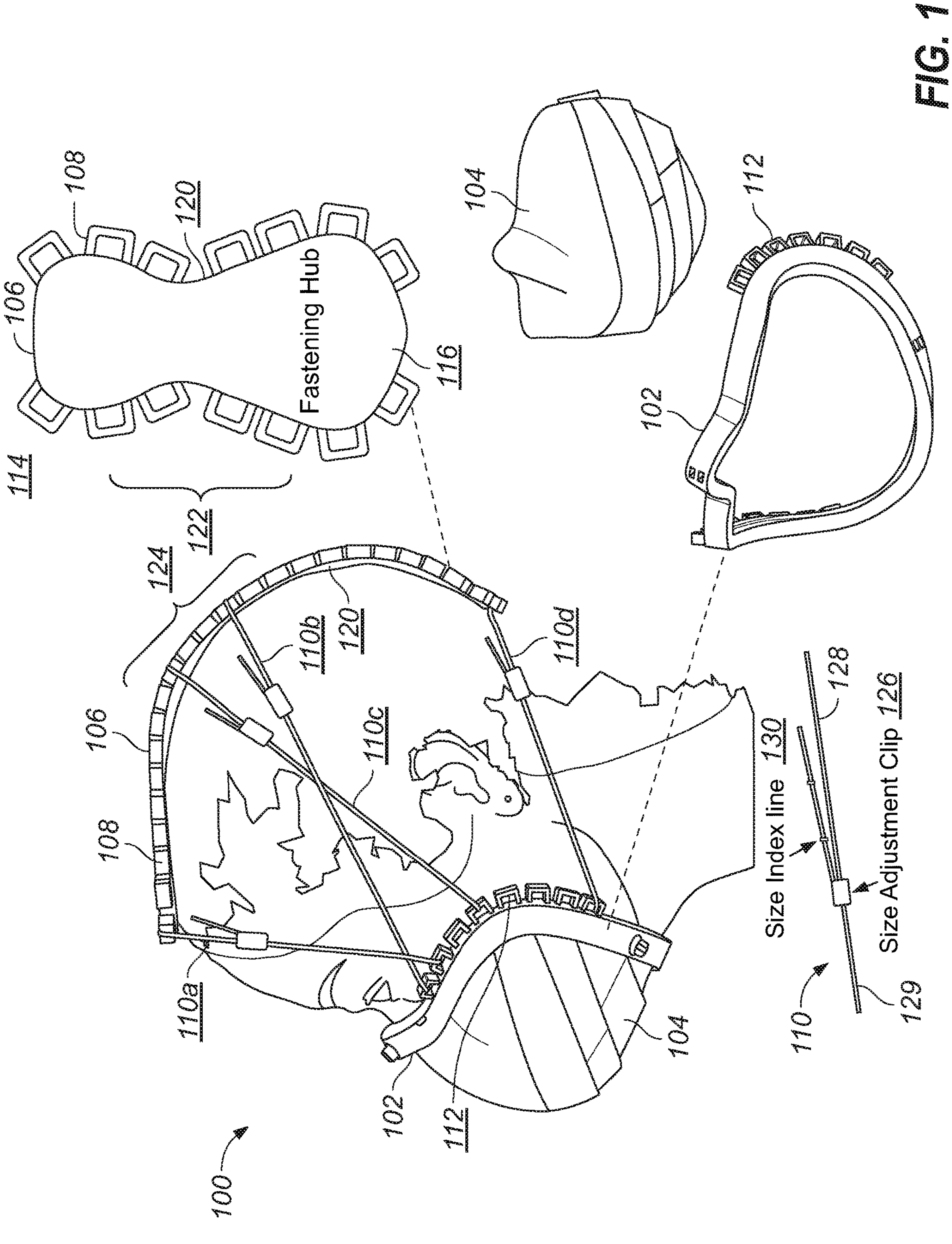
FIG. 1 illustrates an example of a respiratory protective device having a frame for a breathable filter that connects to an attachment supporting apparatus that provides support for the frame in accordance with an illustrative embodiment.

FIG. 1 illustrates an example of a respiratory protective device 100 having a frame 102 for a breathable filter 104 that connects to an attachment supporting apparatus (or, simply, "apparatus") 106 (shown as "fastening hub" in FIG. 1) that provides support for the frame 102. In the example shown in FIG. 1, the attachment supporting apparatus 106 has, along its periphery, a set of anchorable structures 108 (shown as fastening hooks 108') that can bring together one or more straps 110 (shown as 110*a*-110*d*), preferably two or more straps 110, from anchorable structures 112, e.g., fastening hooks 112', distributed on the sides of the frame 102. The supporting apparatus 106 is configured to maintain a pre-defined position of the respiratory protective device 100 over the facial region of the wearer.

As shown in diagram 114, the fastening hub has a support member 116 that forms a solid body, though can be hollow or patterned as described herein, having a contour 120 defining a planar surface having a central hub region 122 to contact and maintain engagement against a parietal region 124 (corresponding to the parietal bone) of a person's head.

The straps 110 are customizable in their number and connection to the anchorable structures 108, 112 and may be adjustable in length to enable the wearer to customize the force/pressure exerted (magnitude and direction) by the frame 102 to optimize fit and comfort. In the example shown in FIG. 1, the straps 110*a*-110*d* each includes an adjustment assembly 126, e.g., the cord lock having a toggle spring stop that can engage or disengage to maintain and adjust the length of one of the strap wire 128. The adjustment assembly is fixably connected to a second strap wire 129. In other embodiments, the strap 110 (e.g., 110*a*-110*d*, etc.) includes a single cord that includes the cord lock. In yet other embodiments, different length straps 110 may be employed.

The strap wire 128, in this figure, includes size index lines 130 that define the overall length of the straps 110. The index may be varied in 1-2 cm or ¼ or ½ inch increments (e.g., any sub-intervals, e.g., 0.2 cm), for example, over a range for a defined population (e.g., adults, kids); other indexing may be used. To this end, in the example shown in FIG. 1, the strap 110*a* may be adjusted to a first length, the strap 110*b* adjusted to a second length, the strap 110*c* adjusted to a third length, and the strap 110*d* adjusted to a fourth length, to allow for uniform force or customized force to be provided by the straps to the frame 102 and the attachment supporting apparatus 106, thus customizing the pressure exerted by the frame 102 and the attachment supporting apparatus 106 on the facial region and back-of-head region of the wear. A wearer can use the size index lines 130 to set the desired length and/or pressure to be provided by the strap to a specific or customized setting.

The anchorable structures 108, 112 extend from the attachment supporting apparatus 106 and the frame 102, respectively. In the example shown in FIG. 1, the anchorable structures 108, 112 are open hooks that extend from the frame 102 or supporting apparatus 106. In other embodiments, the anchorable structures 108, 112 can be holes directly inset within the respective structure. The anchorable structures 108 and 112 for the face and head components may be the same or different.

In FIG. 1, the attachment supporting apparatus 106 includes seven anchorable structures 108 extending from each of its left side and right side. The frame 102 includes eight anchorable structures 112 extending from each of its left side and right side. The number of anchorable structures 108, 112 may be, e.g., two, three, four, five, six, seven, eight, nine, ten, eleven, twelve. The number of structures 108 and 112 may be the same or different. In some embodiments, the number of anchorable structures 108, 112 may be greater than twenty.

In the example shown in FIG. 1, the respiratory protective device is configured as a filtering face respirator (FFR). The filtering face respirator can have filter such as N95, N99, N100, R95, R99, R100, P95, P99, P100, HE filter. The respiratory protective device can be configured as other facepiece respirators or breathing apparatus described herein.

Figure 2A:
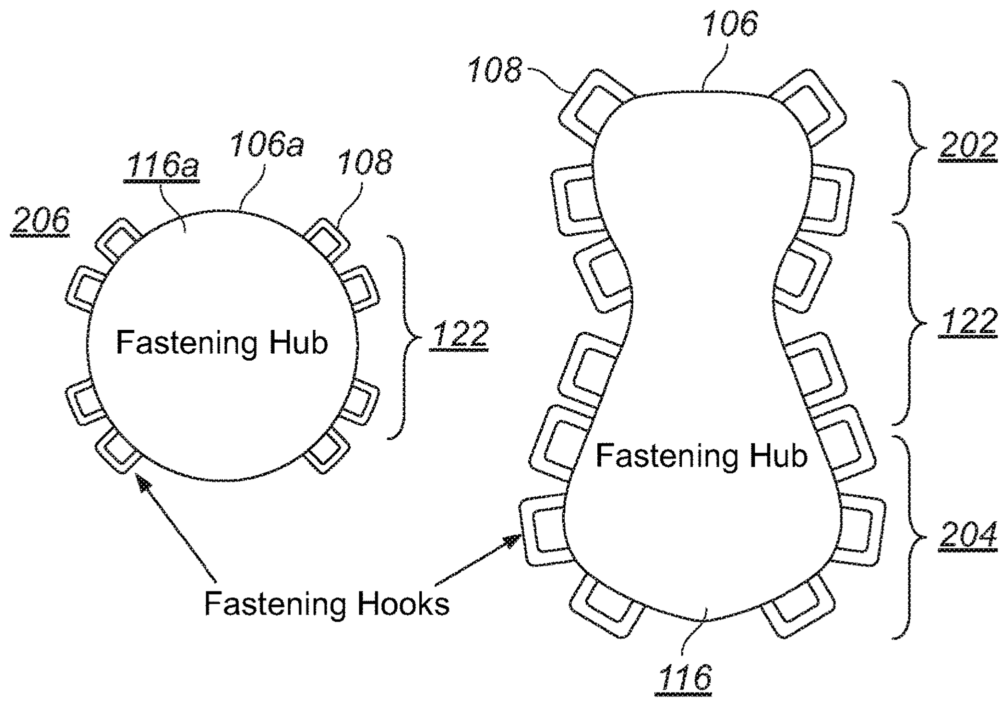
FIGS. 2A and 2B show alternative shapes for the support member for the attachment supporting apparatus in accordance with an illustrative embodiment.
Figure 2B:
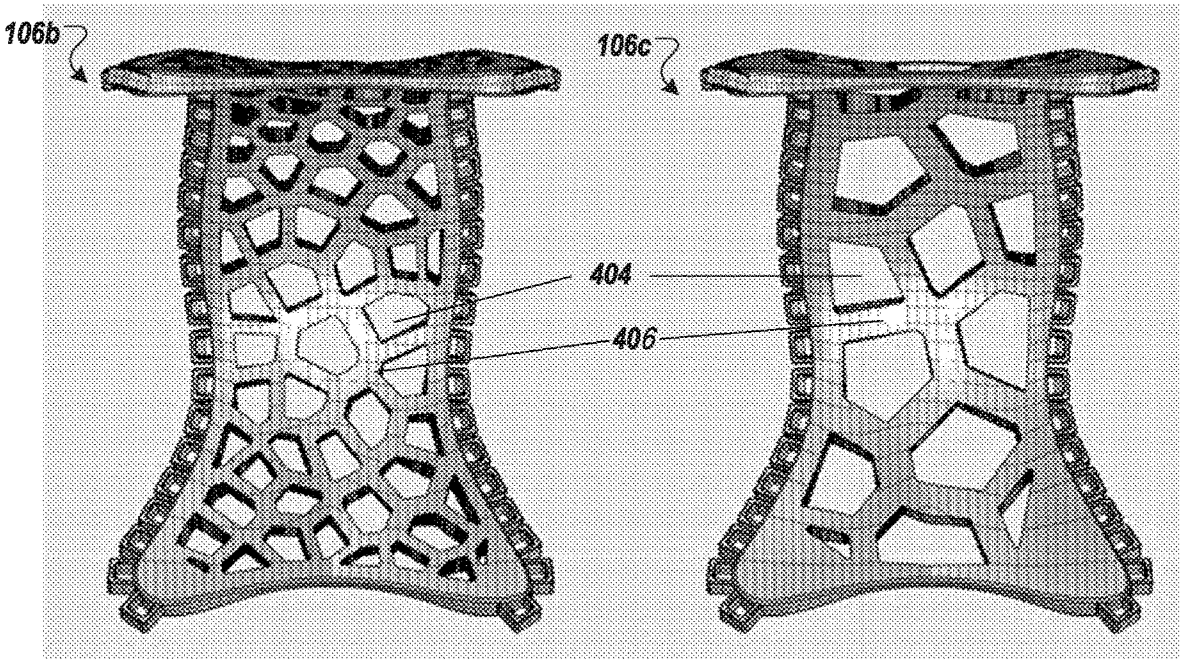

Fastening Hub. FIGS. 2A and 2B show alternative shapes for the support member 116 for the attachment supporting apparatus 106 (also shown as 106*a*). In the example shown in FIGS. 1, 2A, and 2B, the support member 116 has an "hourglass shape" having the narrower central hub region 122 and wider front and back regions 202, 204 that extend therefrom. In diagram 206, the support member 116 (shown as 116*a*) is circular, which defines the central hub region 122 and extends over the parietal region 124 (see FIG. 1).

To reduce the weight of the attachment supporting apparatus 106 and to prevent or reduce heat or sweat build-up under it during use, the attachment supporting apparatus 106 is formed with a plurality of gaps or is formed of a mesh material to provide a lightweight, breathable surface. In some embodiments, the attachment supporting apparatus 106 is formed with a set of pre-defined shapes to define a plurality of struts within its substrate, e.g., forming a tessellation. An example of the tessellation is the Voronoi Tessellation [2]. Tessellation patterns may be generated for a set of parameters, e.g., counts, sizes, and offset percentages of the cells.

In the example shown in FIG. 2B, the tessellated attachment supporting apparatuses 106 (shown as 106*b*, 106*c*) includes a plurality of struts 406 defining a plurality of cells or gaps 404. THe tessellated attachment supporting apparatuses 106 in FIG. 2B include (i) 80 gap counts with a 70% offset and (ii) 20 gap counts with a 70% offset, respectively. The cells or gaps 404 in the tessellation indeed preserved the integrity of the structure with less material volume and were generated using Rhino® with the Grasshopper plugin.

To ensure that the edges with anchorable structures 108 were not cut out, a 5 mm margin was selected on the sides of the supporting apparatus 106*b*, 106*c*.

Figure 3:
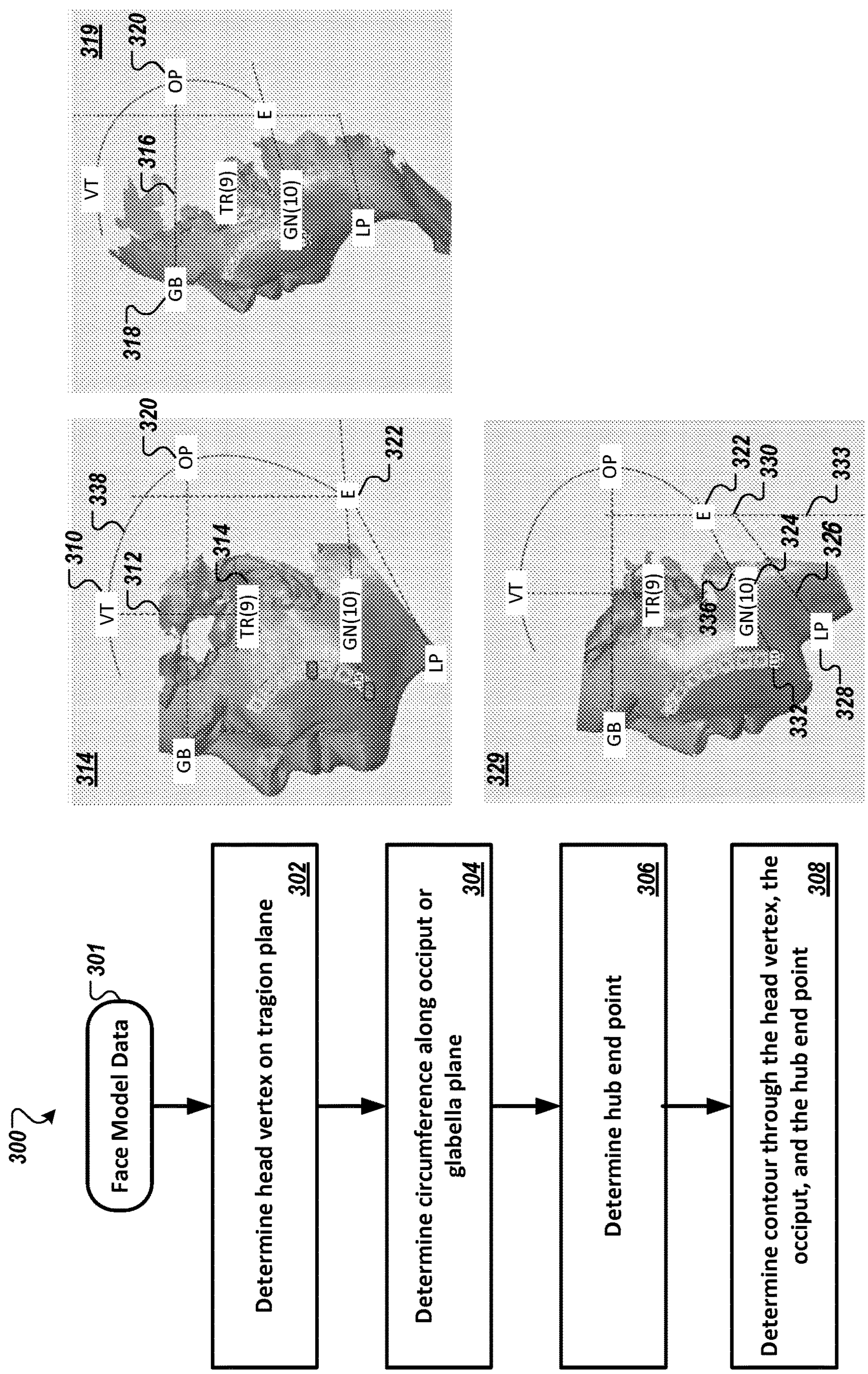
FIG. 3 shows a method to generate a design for a 3D-printable or customized attachment supporting apparatus using anthropomorphic landmarks of the wearer's head.

Example Method to Generate a Customized Respiratory Protective Device with Attachment Supporting Apparatus FIG. 3 shows a method 300 to generate a design for a 3D-printable or customized attachment supporting apparatus, e.g., size and placement, and/or placement and length of straps 110 using anthropomorphic landmarks of the wearer's head.

In the example shown in FIG. 3, the anthropomorphic landmarks include the tragion, the occiput (OP), and the glabella [1]. The vertex is marked "VT", the tragion "TR (9)", the gonion is marked "GN(10)", the occiput "OP," the glabella "GB," the larynx "LP," and the hub endpoint "E," are also marked. Other anthropomorphic landmarks may be employed.

Method 300 includes determining (302) the head vertex 310 and measuring the distance from the vertex along the tragion plane 312 to the tragion landmark 314. See diagram 314. The vertex 310 is on the top of the head, approximately parallel with a vertical line with the tragion 314.

Method 300 includes determining (304) the circumference, via a head circumference measurement, along the occiput and glabella plane 316. See diagram 319. The occiput 318 is parallel to or at about the same level as glabella 320. Description to determine the occiput or glabella may be found in Zhuang, Z., & Bradtmiller, B., "A Head-and-Face Anthropometric Survey of U.S. Respirator Users," J Occup Environ Hyg. November; 2 (11): 567-76 (2005), which is incorporated by reference herein in its entirety. In an alternative embodiment, the Nasion-Occiput distance can be measured.

Method 300 includes determining (306) the hub endpoint "E" 322 as the inion. Because the bottommost fastening strap from the RPD frame must go below the ear to the bottommost hook on the Fastening Hub, Method 304 employed the gonion 324 as a reference point to locate the end (or bottom) point of the hub. Method 304 measures the neck circumference 326 starting from the larynx 328 and uses the diameter to estimate the neck depth. As shown in diagram 329, Method 306 can construct a vertical line 333 at the neck depth point 330, construct a line 336 from the last hook 332 on the RPD frame through the gonion 324 and extend the line 336 until it intersects the vertical line 333. The intersection point (at 322) is the endpoint of the attachment supporting apparatus 106.

Method 300 includes determining (306) a contour 338 (see diagram 314) by interpolating through the head vertex 310, the occiput 320, and the hub end point 322. The contour 338 thus defines the profile of the back of the head for the subject and may define the profile of the attachment supporting apparatus 106.

In some embodiments, the apparatus is customized to a user or a group of users based on images or data from a user or group of users. In order to develop the apparatus 100 and the supporting apparatus 106, an algorithm was developed based on key anthropomorphic landmarks on a user's head. Such a process may be repeatable for a variety of users.

An example process of acquiring a facial scan is provided in U.S. Pat. No. 10,646,731, which is incorporated by reference herein. In FIG. 3B, it can be observed that the vertex 308 is located on the top of the head, approximately parallel with a vertical line with the tragion 310. The method then measures a straight-cut distance from the tragion to the vertex. In other embodiments, Method 300 can locate the vertex by visual inspection and confirmed by palpation.

In some embodiments, the customization and fitting may be described in instructions to allow a person to determine the locations of the head vertex, the occiput, and the hub endpoint and to select an attachment supporting apparatus 106, e.g., from a set of attachment supporting apparatuses having different lengths, e.g., between 5 to 12 inches. The person can select a pre-fabricated attachment supporting apparatus and/or pre-fabricated RPD having similar measurements, e.g., within 1%, within 5%, or within 10%.

Example Strap Connection

Figure 4:
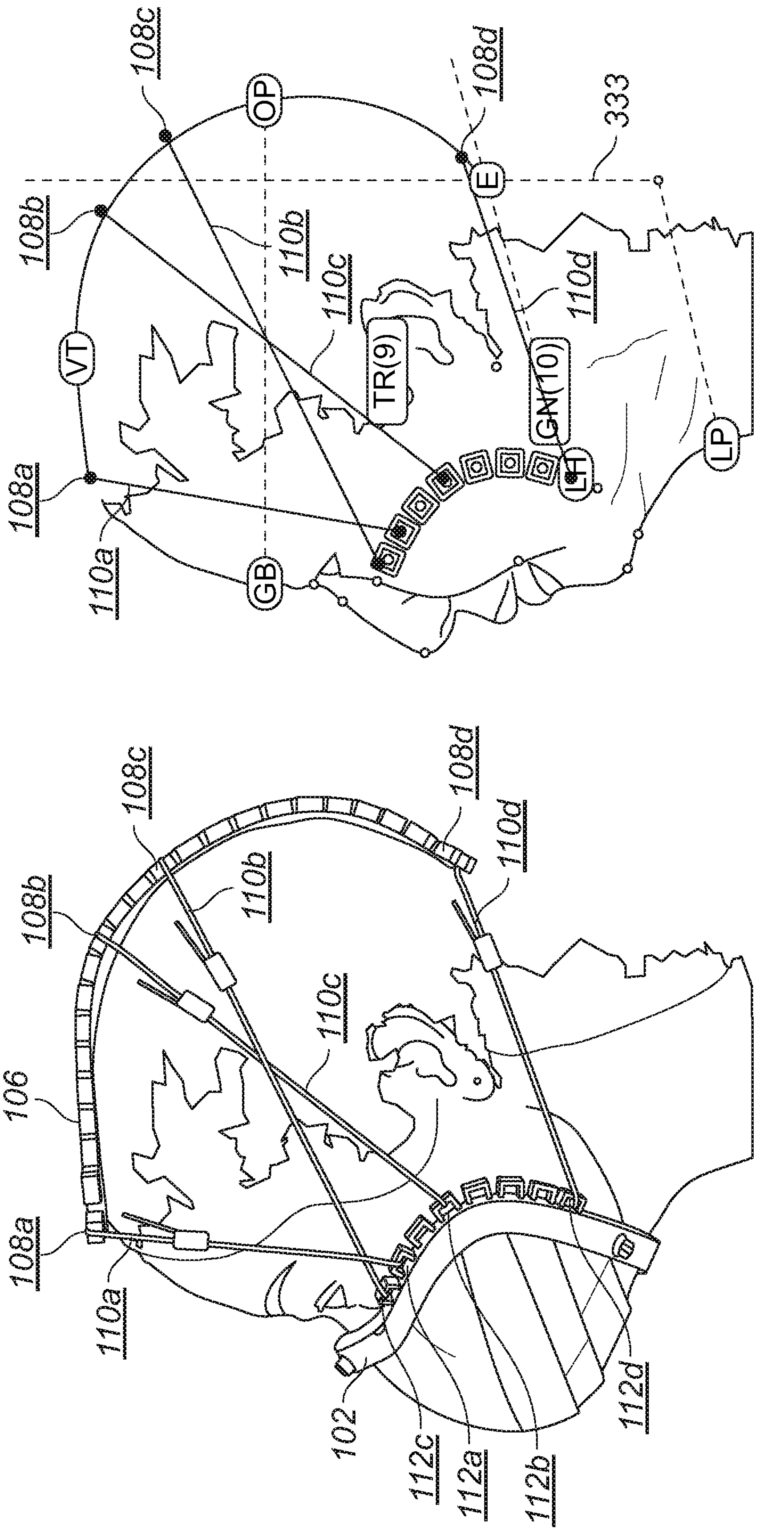
FIG. 4 shows an example method to connect, or configuration of, the attachment supporting apparatus as connected to the frame in accordance with an illustrative embodiment.

FIG. 4 shows an example method to connect, or a configuration of, the attachment supporting apparatus 106 as connected to the frame 102. In the example shown in FIG. 4, the attachment supporting apparatus 106 includes 23 anchorable structures 108, and the frame 102 includes 8 anchorable structures 112.

To provide for the uniform or pre-defined tension and to maintain the straps' orientation and position over several repeated donning and doffing operations, the first head anchorable structure 108*a*, as the leading endpoint structure, is coupled to the second frame anchorable structures 112*a*, shown in this example at structure #2 (112*a*), to maintain the position for the front of the attachment supporting apparatus 106. The second and the third head anchorable structures, located at structures #10 (108*b*) and #13 (108*c*), are generally centered around the parietal region and around line 333 (see FIG. 3) and connect to structures #1 (112*c*) and #4 (112*b*) of the frame 102 in a crisscrossed manner. The fourth head anchorable structure 108*d*, as the trailing endpoint structure, is coupled to the last frame anchorable structure 112*d*, shown in this example at structure #8 (112*d*), to maintain the position for the end of the attachment supporting apparatus 106.

Other configurations for the straps 110 and the attachment supporting apparatus 106 as connected to the frame 102 may be employed.

Example Frame and Filter

Figure 5A:
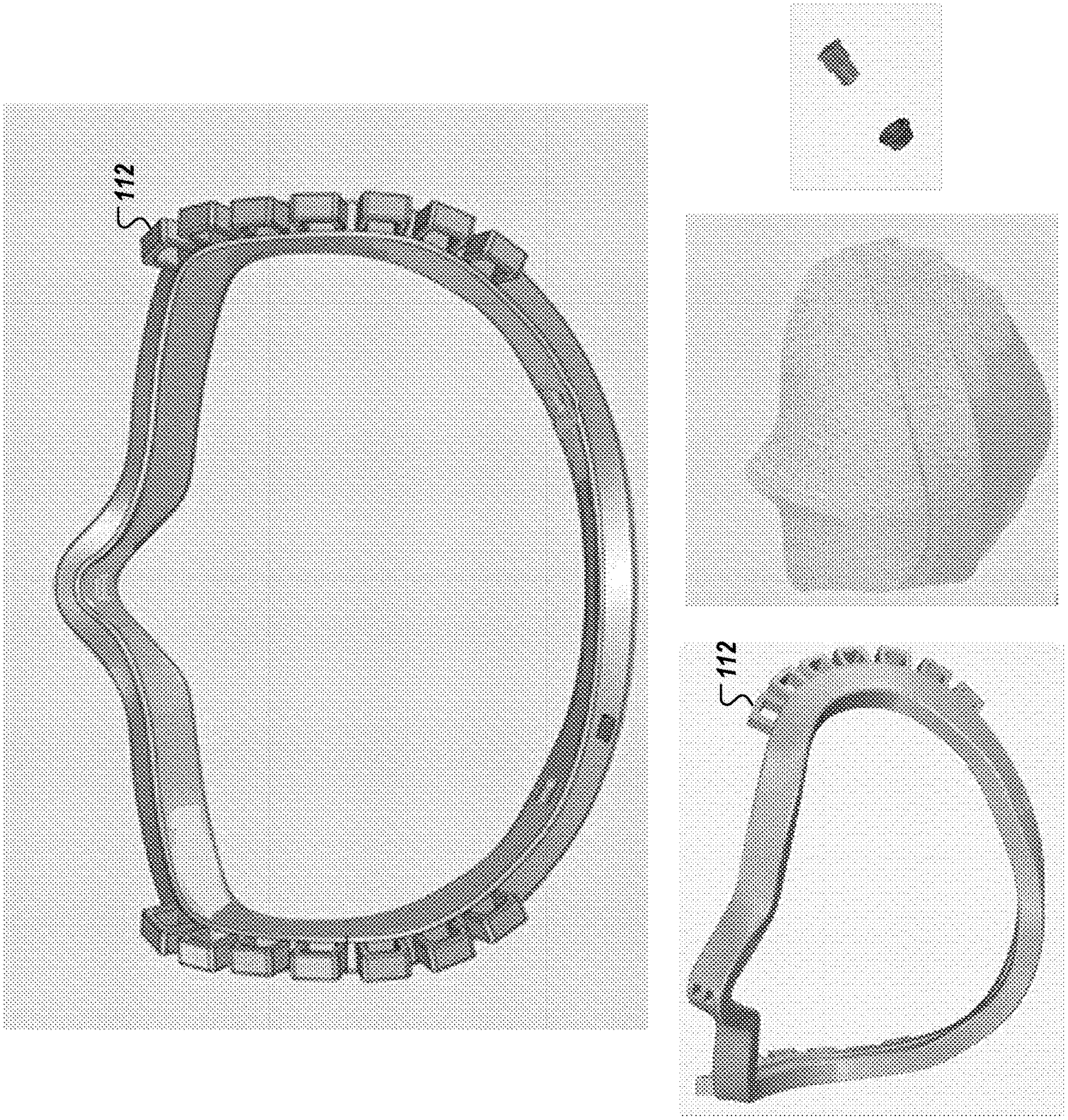

FIGS. 5A and 5B each shows an example frame 102 and filter 104, the frame 102 includes the anchorable structures 112.

As shown in FIG. 5A, each anchorable structure 112 is a hollowed squared box shape structure with rounded/chambered edges. In the example shown in FIGS. 5A and 5B, the outer square edge has a dimension of 10 mm with a corner radius of 1 mm, while the inner square edge is 6 mm with a corner radius of 1 mm. The thickness of each anchorable structure 112 is 6 mm.

FIG. 5B shows details of an example design of the anchorable structures 112. From the zygomatic landmark ("8") (see FIG. 7C), the midpoint "H1" for the structure 112 may be defined and spaced apart by 12 mm. Each structure 112 may be superimposed over the midpoint "H1".

Additional description of the frame may be found in U.S. patent application, Titled "CUSTOM-FIT REUSABLE RESPIRATORY PROTECTIVE DEVICE," concurrently filed herewith, having U.S. application Ser. No. 18/162,315, which is incorporated by reference herein in its entirety.

The frame may be configured with sensors, e.g., as an integrated sensor-integrated respiratory protective device. Additional description of the sensor and integration may be found in U.S. patent application, entitled "RESPIRATORY PROTECTIVE DEVICE WITH CONTINUOUS FIT MONITORING," concurrently filed herewith, having U.S. application Ser. No. 18/162,312, which is hereby incorporated by reference herein in its entirety.

Sensor or Electronic Integrated Attachment Supporting Apparatus

Figure 6A:
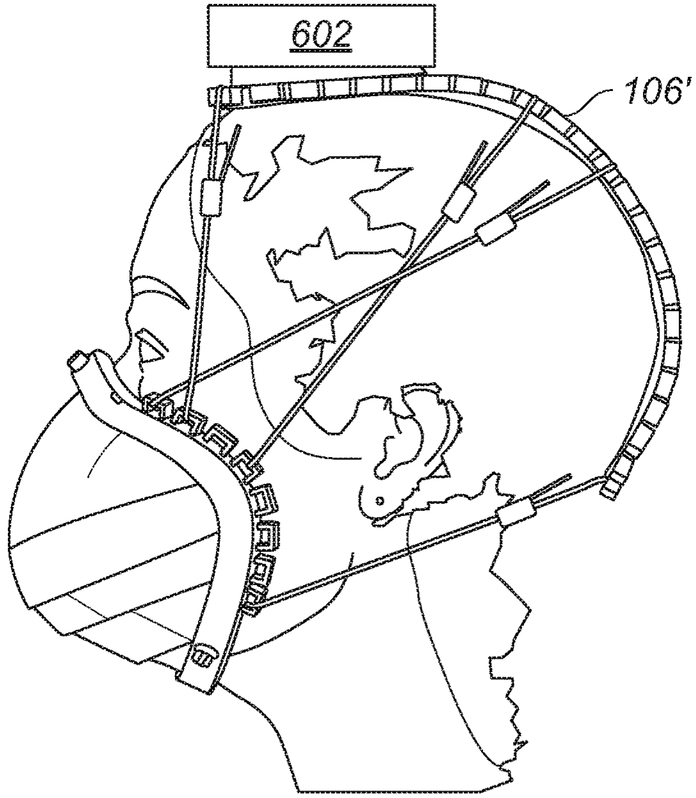
FIGS. 6A and 6B each shows a configuration of the attachment supporting apparatus with an external or integrated component in accordance with an illustrative embodiment.
Figure 6B:
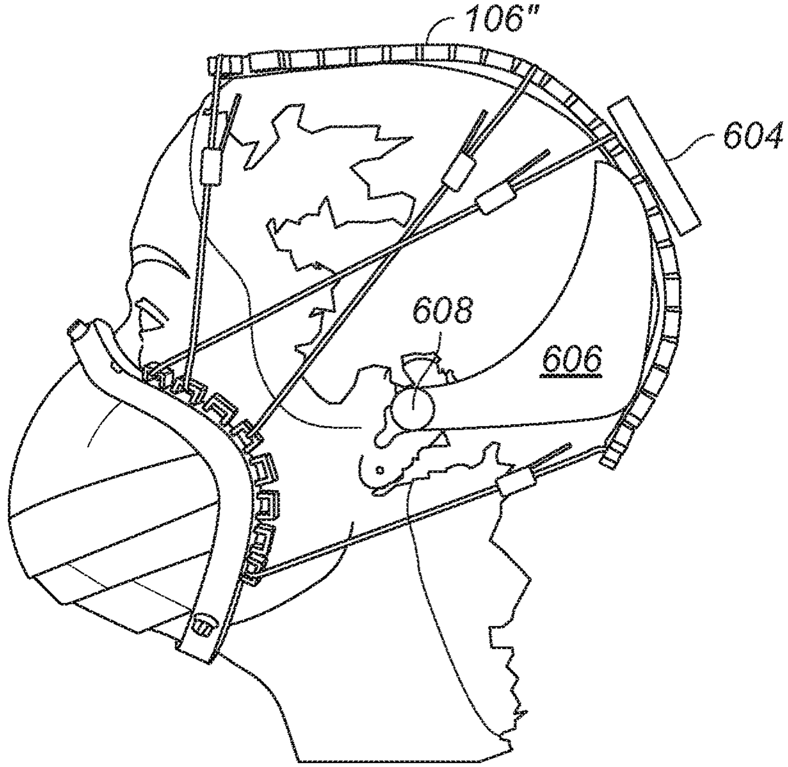

In another aspect, the attachment supporting apparatus 106 can serve as a platform for the attachment of other devices including, but not limited to, a flashlight or handheld electric lamp, a microphone, a speaker, and/or a computing or electronic device (e.g., smartphone), e.g., to enable hands-free use. FIGS. 6A and 6B each shows a configuration of the attachment supporting apparatus 106 with an external or integrated component. In FIG. 6A, the flashlight or handheld electric lamp (602) is shown integrated into the attachment supporting apparatus 106 (shown as 106'). The attachment supporting apparatus 106 may provide a pocket to retain the flashlight or handheld electric lamp. In some embodiments, the attachment supporting apparatus 106 includes holes for attachments of a binding that can bind the flashlight or handheld electric lamp to the attachment supporting apparatus 106.

FIG. 6B shows another configuration of the attachment supporting apparatus 106 (shown as 106") configured with an integrated electronic component such as a microphone, a speaker, and/or a computing or electronic device. In the example shown in FIG. 6B, the electronic components 604 are integrated into a pocket defined in the attachment supporting apparatus 106. Description for designing a frame with pockets sensors may be similarly employed for integration of electronic components, as described in U.S. patent application, entitled "RESPIRATORY PROTECTIVE DEVICE WITH CONTINUOUS FIT MONITORING," concurrently filed herewith, having U.S. application Ser. No. 18/162,312, which is hereby incorporated by reference herein in its entirety. The channels/conduits for routing of various wirings for the electronic components are also provided therein.

In the example shown in FIG. 6B, the attachment supporting apparatus 106 comprises a thin extension member 606 that provides routing of cabling to the ear, e.g., having a speaker 608.

Experimental Results and Additional Examples

A study was conducted to design and develop a custom-fit reusable RPD. The developed custom-fit reusable RPD can be customized using facial scanning or facial fitting. The RPD was designed to facilitate easy replacement of the filter and decontamination of the frame after every use. By facilitating the customization of the RPD-ensuring the right fit and choice of the filter with the desired degree of filtration—the custom-fit reusable RPD can be used for adults and children. The study analyzed facial features and anthropometry in the design of the custom-fit RPD.

The study also developed an attachment-supporting apparatus that can be used in conjunction with the custom-fit reusable RPD.

Selection of Anthropometric Facial Landmarks. The study evaluated human facial anthropometrical data, including anatomic landmarks, dimensions, and contours that define an individual's facial profile in designing a custom-fit RPD. These anthropometric characteristics were used as "references" for customizing the RPD for any facial profile. An initial challenge lies in identifying the right set of these anthropometric facial landmarks. The NIOSH study, which had identified 26 pre-defined landmarks and 21 facial dimensions, was used as the starting point [13]. The present study selected an initial 18 of the 26 facial landmarks from the NIOSH study focusing on the lower face (below the nasal root points since the proposed device is analogous to a half-facepiece respirator).

Among these selected landmarks, some are not directly relevant to the purpose of measuring either the face size or the base frame shape but serve as reference points that can help better position and orient the face images in horizontal and vertical planes. For example, the pupils, pronasale, chellions, and tragions can assist with balancing the symmetry for the facial image. The black landmarks in the figure aid in positioning, orienting, centralizing, and symmetrizing the scan data and mappings. The landmarks "3," "7," and "8" fall on the contour of the frame.

Figure 7A:
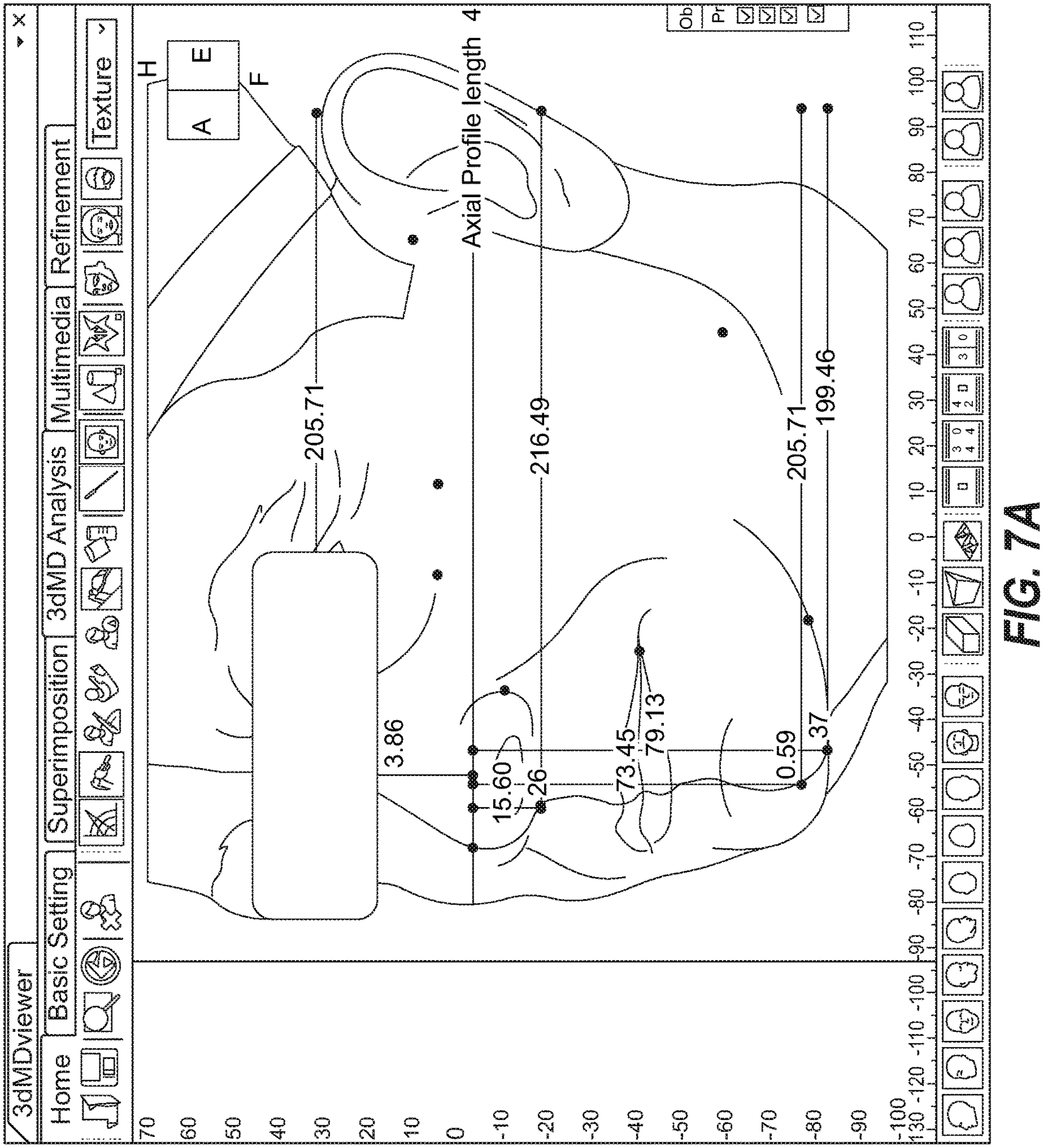
FIGS. 7A-7H show various aspects of a study conducted to develop a respiratory protective device with the exemplary attachment supporting apparatus in accordance with an illustrative embodiment.
Figure 7B:
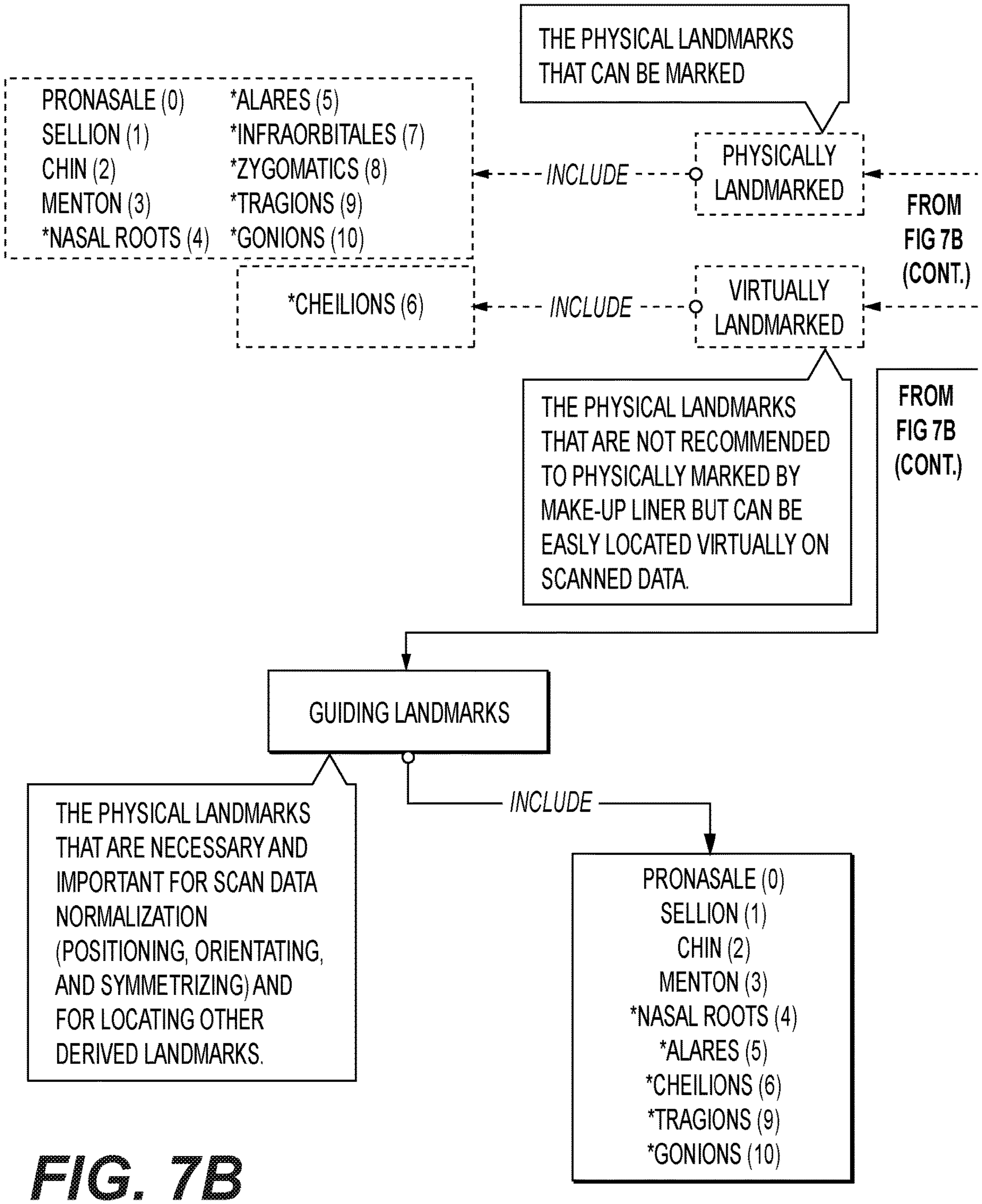
Figure 7B:
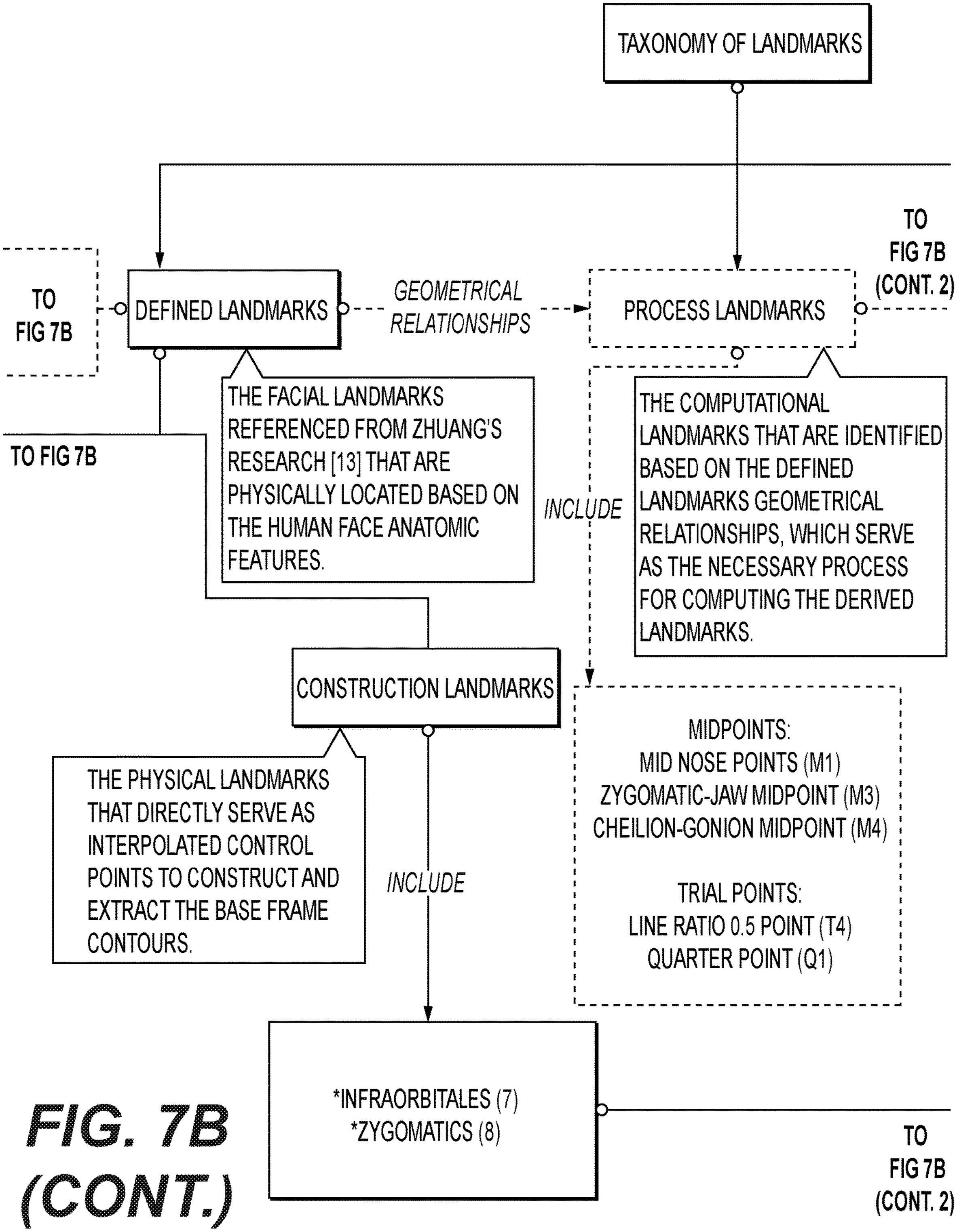
Figure 7C:
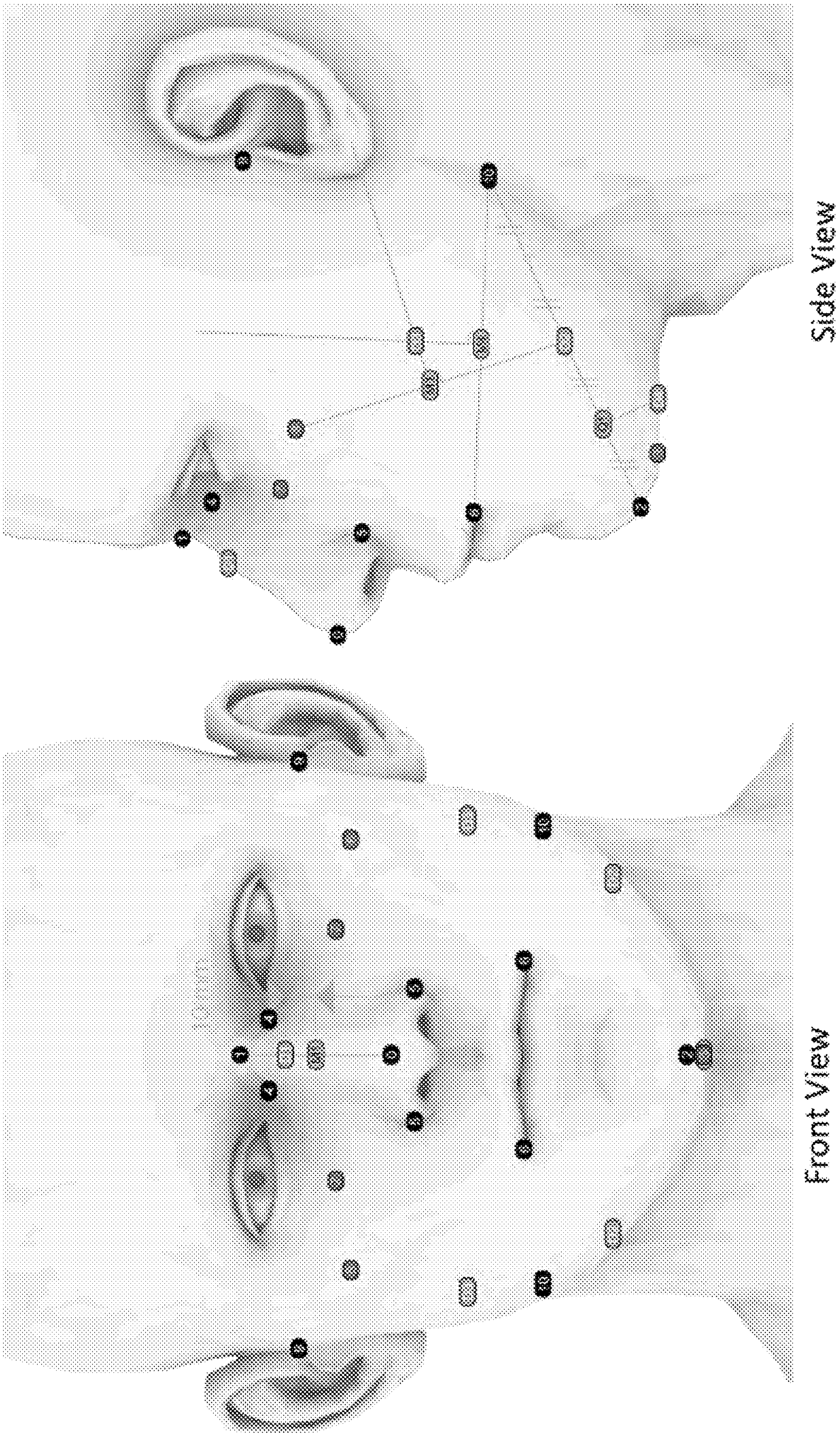

In addition to selecting the landmarks, specific dimensions were identified that must be measured to characterize the facial profile. The study employed 15 facial dimensions, six of which are from the NIOSH study's 21 facial dimensions; the others were identified specifically for creating a customized RPD. Eleven of these dimensions were straight-cut distances from point to point. The remaining four dimensions were straight-cut vertical ratio measurements, which, similar to reference landmarks, are reference proportion lines for positioning and orienting. FIG. 7C shows the selected facial landmarks and the various dimensions employed for the design.

3D Scanning and Customized Frame Contour Development: For developing the customized RPD, the study developed a design framework that took a 3D scanned image, put it into a 2D framework for the analysis, which was then projected back to the 3D space for 3D-customized printing of the frame.

The study developed customized RPD for three participants (2 females and 1 male) with different facial profiles. The study used the 3dMD System for scanning the facial profiles [14]. The 3dMD face scanner captured the three-dimensional face image from ear to ear. The system employed manual labeling of the facial anthropometrical and anatomical landmarks. Before scanning, the subject was physically marked with a red lip liner at the facial landmarks. For the 3D scan, the participants were asked to look straight and relax their facial expressions while the 3D cameras recorded a 10-second footage with over 100 scan frames. The exported files for each participant contained all the frames in an OBJ file format with colored textures. The landmarks were seen clearly on the faces. It was observed that the 10-second footage could provide selectable images from the multiple frames in which the selected image was without blurs or noise due, e.g., due to the inevitable shaking, swinging, or blinking that may occur during the scanning.

The study used 3dMD Vultus, a native software for the 3dMDface™ System, to process the scanned image. The study virtually re-marked in the software the landmarks and measured their dimensions. The study applied different tools (plane cut, mask, and refinement) to cut off the unwanted debris and fragments (e.g., hair texture) to focus on the front face area. The core task was to use the measurement and analysis tools to digitize the landmarks and dimensions.

The study developed landmark and dimension analysis scripts to analyze the scanned profiles of the subjects for the landmarks and dimensions. With the available landmark and analysis (dimension) scripts, the points were overlaid onto the physical landmarks and placed marks onto the non-contactable landmarks (e.g., pupils). In the built-in world coordinate system, each landmark had a coordinate (x, y, z), and the origin (0, 0, 0) was placed at the pronasale point as the center reference point on the face. The other landmarks were accordingly updated to their new coordinates. This helped to understand the overall relationship between all the landmarks easily and quickly. Subsequently, the analysis script automatically generated a report file for all the dimensions measurements needed. FIG. 7A shows the scanned images of one of the participants in 3dMD's Vultus program.

A Taxonomy of Landmarks: A study proposed taxonomy for the set of facial landmarks for developing the custom-fit RPD. As shown in the chart illustrated in FIG. 7B, the defined landmarks are those obtained from literature and serve as the basis for identifying additional landmarks for developing the contour of the RPD frame. These defined landmarks were classified into guiding landmarks and construction landmarks. The guiding landmarks guide the design of the customized frame; for example, pronasale (0) served as the origin (0, 0, 0) for the computations. The construction landmarks were used for constructing the final contour of the frame. The various intermediate landmarks that served to develop the final set of landmarks-based on geometrical relationships with the defined landmarks-were called process landmarks. These process landmarks were used to derive the derived landmarks. Thus, the customized frame contour was constructed using the construction landmarks and derived landmarks.

This taxonomy has a critical role to play in designing and developing a custom-fit RPD to fit any facial profile. The derived landmarks were based on defined steps (algorithms) drawing upon the defined landmarks as the foundation. Therefore, the process of creating a customized contour for any facial profile can be automated using the algorithms underlying the taxonomy shown in the figure. FIG. 7C shows the locations of the various facial landmarks in the taxonomy.

Figure 7D:
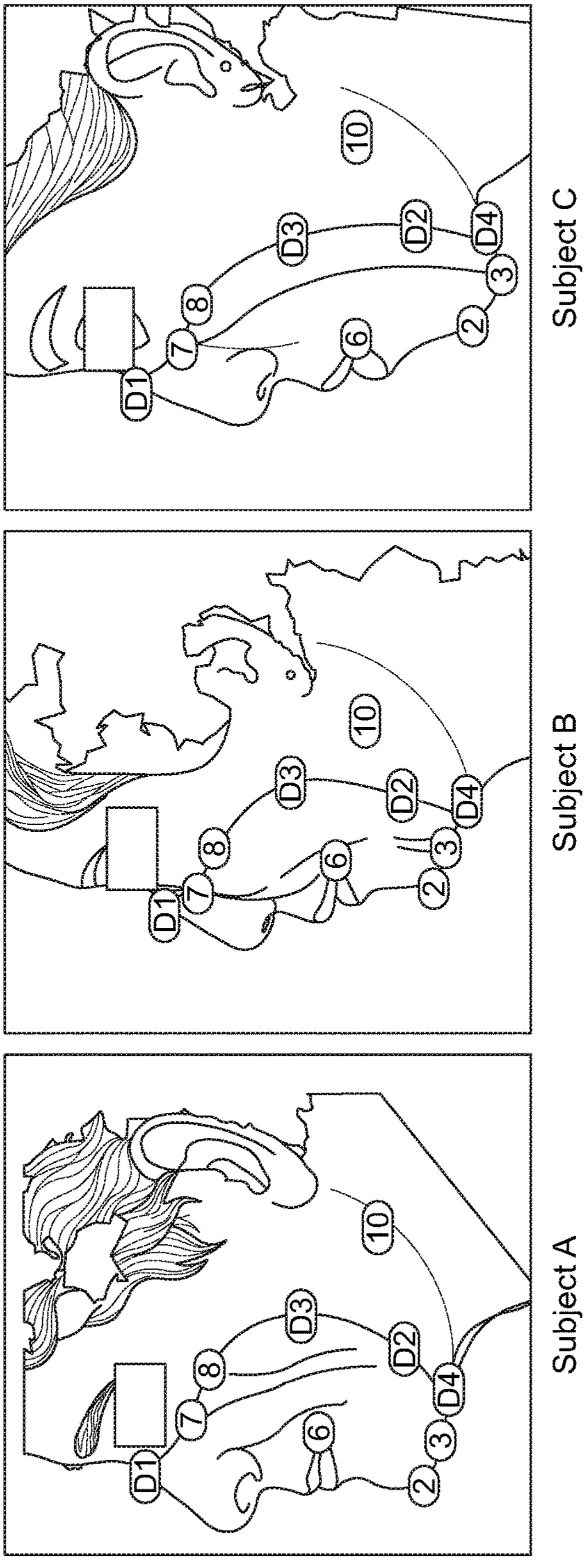
Figure 7E:
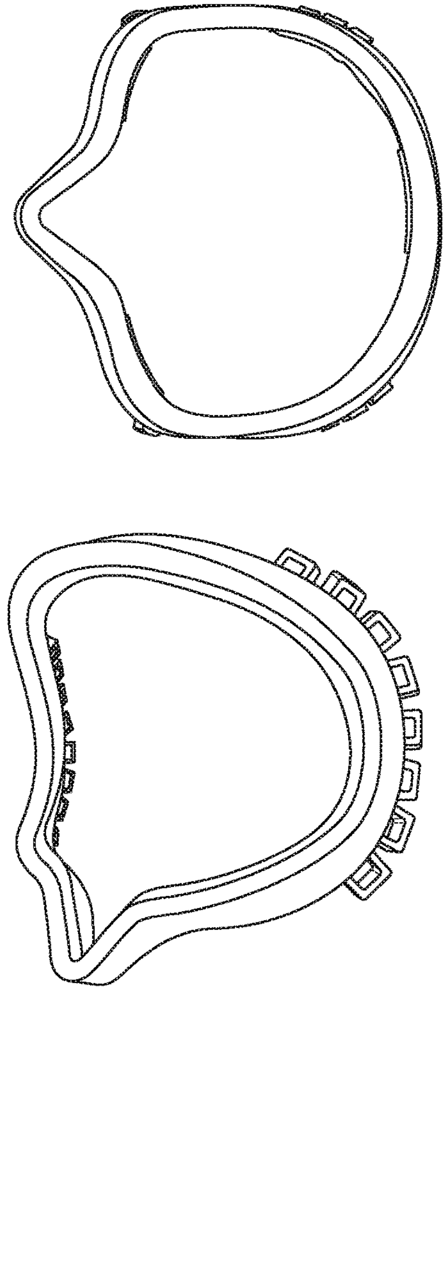
Figure 7F:
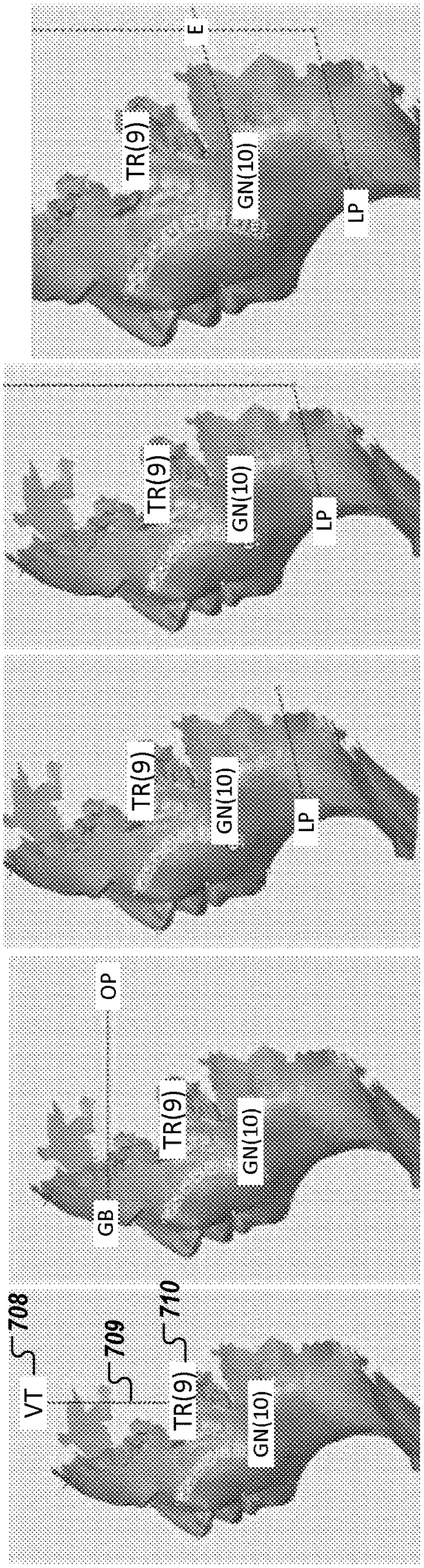
Figure 7G:
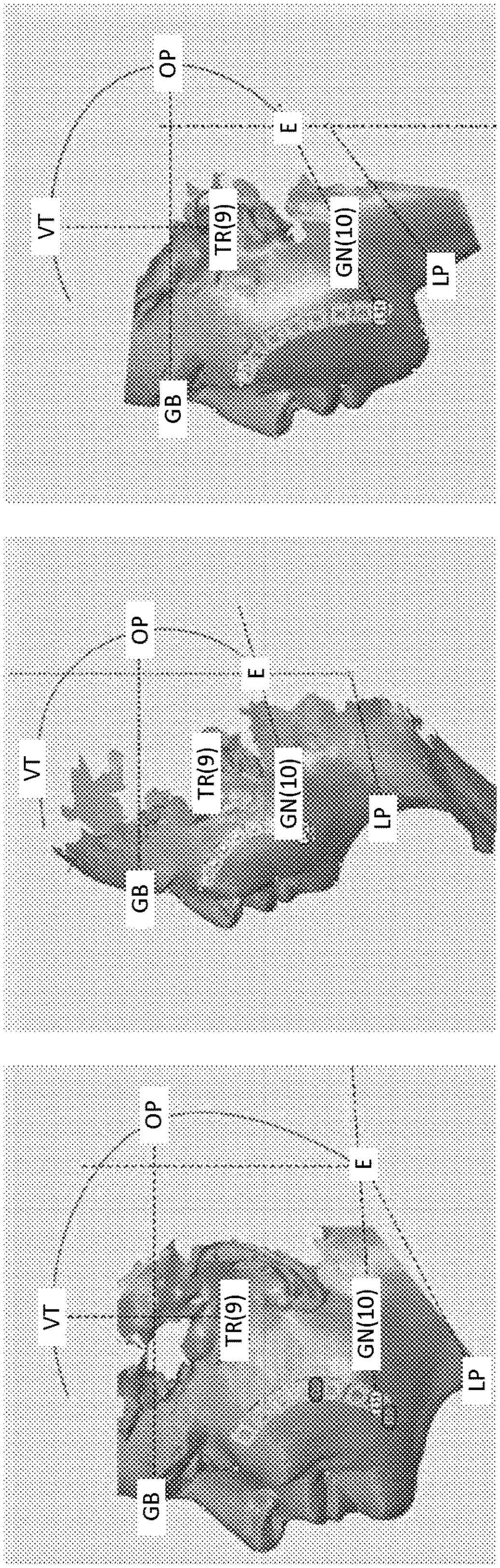

Defining a Taxonomy of Landmarks. The study imported the textured scanned data into Rhino® CAD software to construct the 3D model of the RPD frame. With the pronasale point as the origin of the coordinate system, the study mapped out the other landmarks by placing the exact three-dimensional coordinates in the Rhino software coordinate system. The first step in the "3D to 2D to 3D" design methodology is "3D to 2D. The study performed a geometrical projection of all the three-dimensional landmarks onto a two-dimensional plane that is parallel to the coronal plane to provide 2D mapping that employs all the landmarks with their relationships in lateral (horizontal or Y-axis) and medial (vertical or Z-axis) directions.

relation to FIG. 3. FIG. 7F shows the process of generating a customized attachment supporting apparatus for one participant of the study or an attachment-supporting apparatus suited for the dimension of that participant. FIG. 7G shows the landmarks and derived measurement for three participants, e.g., to be used with the RPD having the contour determined in FIG. 7D.

Figure 7H:
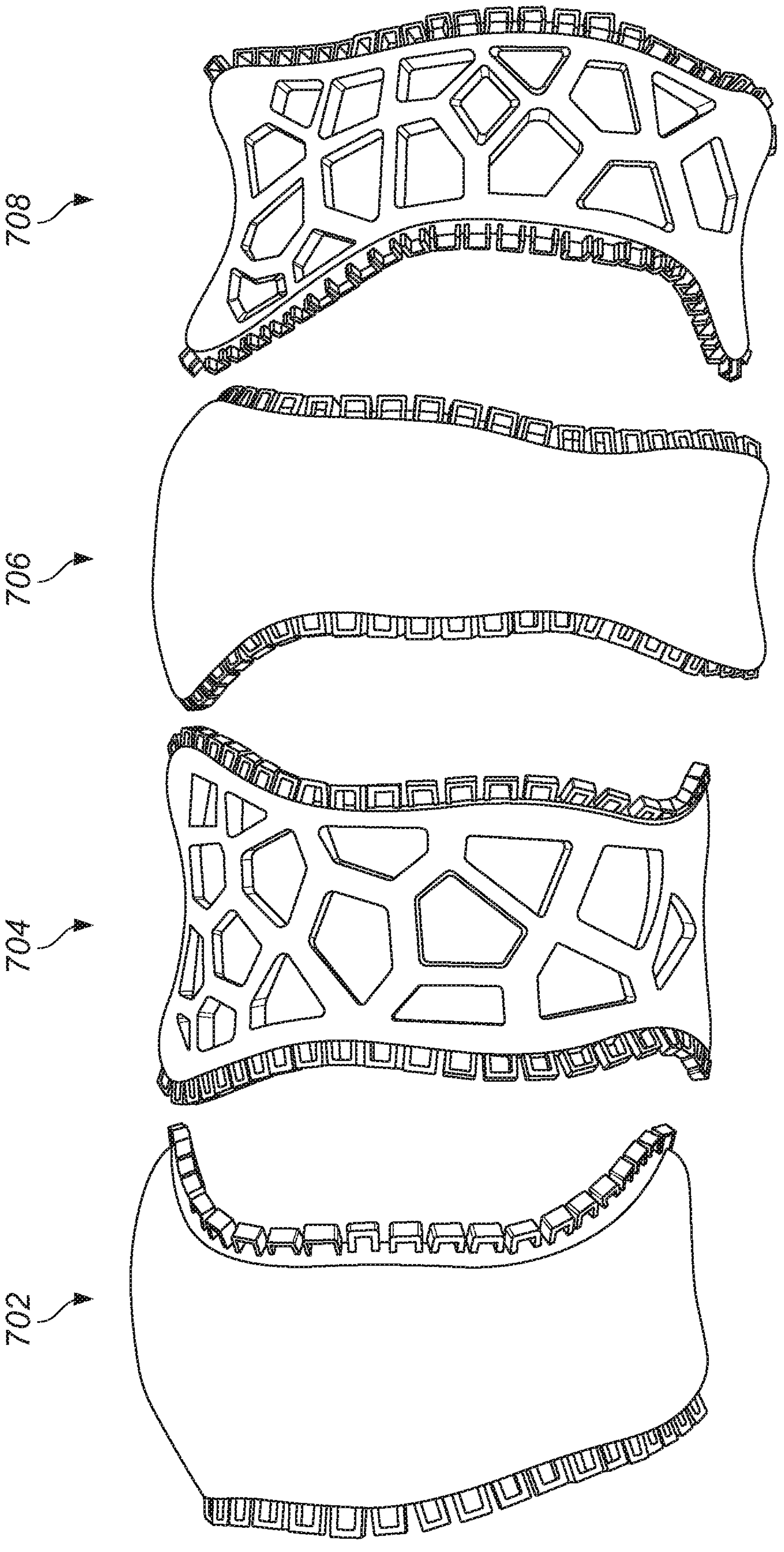

Example Fabricated Attachment Supporting Apparatus. FIG. 7H shows embodiments of the attachment supporting apparatus 106 created using a 3D printer. The devices are formed of a polylactic acid (PLA) material on a fused deposition modeling (FDM) printer. In FIG. 7H, device 702 is printed with PLA; device 704 is printed with PLA with Voronoi tessellation; device 706 is printed with Elastic 80A without Voronoi tessellation; device 708 is printed with Elastic 80A with Voronoi tessellation.

Material. Table 1 shows the properties of silicone-based materials, e.g., that can be used for 3D printing of the frame and device components described herein, e.g., frame 102 and the attachment supporting apparatus 106: Elastic 50A [18], SIL30 [19], SILASTIC 3D 3335 LSR [20], and AMSil [21].

TABLE 1

| Manufacturer | Material | Tensile Strength (MPa) | Tear Strength (kN/m) | Elongation @ Break (%) | Shore Hardness (A Class) | Material Type |
|---|---|---|---|---|---|---|
| Formlabs | Elastic 50A | 3.23 | 19.1 | 160 | 50 | Silicone Urethane Elastomer |
| Formlabs | Elastic 80A | 8.9 | 11 | 120 | 70 | Silicone Urethane Elastomer |
| Carbon 3D | SIL 30 | 3.5 | 10 | 350 | 30 | Silicone Urethane Elastomer |
| DOW | SILASTIC 3D 3335LSR | 8.3 | 0.05 | 5.25 | 50 | Liquid Silicone Rubber |
| Elkem | AMSil | 2 | 10 | 200 | 70 | Engineering Silicone |

The study then augmented the chosen facial landmarks in FIG. 5C with landmarks on the side of the face and the jaw area for drawing a smooth contour of the RPD frame. The "3D to 2D to 3D" design framework was followed to project all the pre-defined physical landmarks onto both the front view 2D plane and the right-side view 2D plane. This provided a better understanding of the numerical and geometrical relationships of the landmarks and facilitated the identification of new ones for drawing the smooth contour of the RPD frame. This initial set of landmarks termed "Defined Landmarks," did not provide a smooth contour of the entire RPD frame. Therefore, the study developed algorithms to identify new landmarks on the front view 2D mapping. These new landmarks are "derived" based on the Defined Landmarks and are named "Derived Landmarks."

Description of the derived landmarks may be found in U.S. patent application, titled "CUSTOM-FIT REUSABLE RESPIRATORY PROTECTIVE DEVICE," concurrently filed herewith, having U.S. application Ser. No. 18/162,315. FIG. 7D shows the base frame contour for the RPD for three different subjects. FIG. 7E shows a fabricated frame for a respiratory protective device.

Attachment Supporting Apparatus. The study developed processes to design and fabricate an attachment supporting apparatus. The study employed the method discussed in In evaluating the materials, the study determined the shore hardness to be a property of interest because the respiratory protective device should be soft on the user's face. After a comparative analysis of the properties, the study decided that Elastic 50A and SIL 30 were potential candidates for creating the physical prototypes of the frame 102 because their Shore A hardness was in the 30-50 range. Even though the Shore A hardness of Silastic from Dow was 50, its tear strength was only 0.05 kN/m, which was very low compared to the other two materials. Both SIL 30 and Elastic 50A are also compatible with cleaning solvents used for decontamination, including, but not limited to, bleach (NaClO, 5%), Sanitizer ($NH_4Cl$, 10%), or solvents for elastomeric respirators, and UV radiation. Since the supporting apparatus 106 will be mounted on the user's head, it must conform to the shape of the head while simultaneously being soft on the head and strong. Unlike the frame 102, the supporting apparatus 106 is not subjected to cyclical changes during regular use of the respiratory protective device. For this reason, Elastic 80A from Formlabs was chosen as a potential candidate for printing the supporting apparatus 106 on Form 3 printer from Formlabs. Elastic 80A is also compatible with cleaning solvents used for decontamination, including, but not limited to, bleach (NaClO, 5%), Sanitizer (NH4Cl, 10%), or solvents for elastomeric respirators, and UV radiation.

DISCUSSION

Protection of healthcare workers in the event of an influenza pandemic is a national imperative, and personal protective equipment (PPE) is at the frontline of defense. The COVID-19 Pandemic has reinforced the importance of personal protective equipment, especially reusable respirators, for healthcare workers on the frontlines [12, 13, 14].

The three key challenges associated with using N95 respirators are the need to "fit" the respirator to the wearer, the annual fit-testing, and reusability. To address these challenges, the concept of scanning an individual's face and creating a customized respirator frame into which a replaceable filter of desired protection level (e.g., N95) could be integrated was developed and led to a US patent [15]. Two straps are currently used to secure an N95 FFR onto the wearer's face. The pressure exerted by the RPD on the face at the interface affects both the comfort of the wearer and the leakage at the interface, the faceseal. There is a critical need for a way to don the RPD properly, quickly, easily, and repeatable manner.

The exemplary system and method can bring together the straps from the fastening hooks distributed on the sides of an RPD; the hub is placed preferably on the back of the user's head. The strap lengths are adjustable to enable the user to customize the force/pressure exerted (magnitude and direction) by the RPD and thereby optimize fit and comfort. The methodology includes algorithms to customize the fastening hub for individuals based on a set of head anthropometric landmarks. Optionally, a calibration scale built into the straps will enable the user to position the straps quickly, which will be critical when access to respiratory protection is needed at short notice. The hub can also preserve the orientations and positions of the individual straps from the fastening hooks to ensure uniform fit around the face. The digital prototypes have been transformed into physical prototypes with additive manufacturing using a silicone-based polymer and other materials.

Roberge et al. studied the importance of tethering devices that hold the RPD on the face on repeated doffing and donning [16]. They found "a progressive decline in the loads generated by the top and bottom tethering devices of the three models of N95 FFR tested over the course of multiple simulated donning, doffing, and wear periods in a 2.5-hr span." This change in load (and hence, pressure) on the face seal could alter the "fit" of the respirator leading to leakages and thereby compromising the degree of rated protection from the device.

In addition to the elastic properties of the straps, the pressure exerted (both in magnitude and direction) at the interface of the face and the RPD depends on how the straps are positioned (e.g., distance and angle) on the wearer's face and head. Each time the RPD is worn, the straps are likely to be in a different position, thereby affecting the pressure and, consequently, the fit, which in turn affects the degree of protection to the user. Furthermore, there is no provision to "adjust" the force exerted by the straps based on the wearer's facial profile and/or head size. In short, it is challenging for the user to place the straps in the ideal positions that will effectively balance fit, viz., protection and comfort. Therefore, there is a need for a mechanism to ensure that the user dons the RPD quickly, easily, effectively, and in a repeatable manner.

The exemplary system and method can serve another purpose, especially in high-risk environments, such as hospitals treating COVID-19 patients in isolation units. Wireless communications devices and battery-operated lights can be attached to it to provide an additional dimension of protection to the user, e.g., a health care professional, when they cannot come out of the isolation unit and need access to "hands-free" communications devices to avoid spreading the infection through contact.

Facial Features and Anthropometry. The shape of the human face is complex and diversiform due to a multitude of reasons, including gender, ethnicity, and demographics [22]. Zhuang and Bradtmiller (2005) developed and proposed a fundamental and universal measuring approach for head-and-face anthropometry [3]. This study surveyed the head-and-face anthropometrical measurements among U.S. respirator users, including over 3997 samples, and covered three major ethnicities in the U.S. (Caucasian, African American, and Hispanic), the majority of age ranges (from 18 to 66), and both genders. The captured head-and-face size distribution among the U.S. population includes 26 landmarks and 21 dimensions. These landmarks and dimensions cover both face size evaluation and head size. These have been valuable for manufacturing filtering facepiece respirators (FFRs) since they can help categorize size ranges and aid in fitting them to users. In their study on fit panels, Zhuang et al. (2008) quantitatively analyzed respirator size fit for different users in terms of pre-defined size ranges [23]. They found outliers and improper fit in small and large size ranges. Lin and Chen (2017) investigated the effect of the FFR style on the fit experience of an Asian population [24]. They used the Cup, Fold, and Liner FFR models, which have distinct edge contours, in the study. Based on the fit panel test and data analysis, they concluded that the Fold model fit significantly better than the other two models for medium and large Asian facial size groups [24]. Therefore, today's practice of producing FFRs in standard sizes based on a grading system limits users' options and leads to challenges with fit and comfort, thereby potentially compromising the degree of protection for users.

A respiratory protective device (RPD) is defined as any personal device that provides protection against inhalation hazards when used effectively, acknowledging that each device may offer either personal protection or source control, or both at varying levels [25]. Jayaraman and Park (2020) proposed the concept of scanning an individual's face to create a custom-fit respiratory protective device (RPD) frame with a replaceable filter of desired protection level (e.g., N95) [15]. After use, the filter would be discarded, the RPD frame decontaminated, and rendered ready for use with a new filter.

The complexity of the diverse human face shapes requires a better and more flexible method to design, as described herein, an RPD customized to a user's facial features. The RPD should also facilitate the use of filters with desired filtration efficiencies depending on the degree of protection needed against specific inhalation hazards. The RPD should be reusable to address the supply chain shortages witnessed during the onset of the COVID-19 pandemic. Therefore, the design should facilitate the replacement of the filter and easy decontamination of the RPD frame after each use. By harnessing advanced technologies, including 3D scanning and additive manufacturing, as described herein, for the development of a reusable RPD, the fit experience can be enhanced, and the long-standing issues with today's mass-produced FFRs can be addressed.

It must also be noted that, as used in the specification and the appended claims, the singular forms "a," "an," and "the" include plural referents unless the context clearly dictates otherwise. Ranges may be expressed herein as from "about" or "5 approximately" one particular value and/or to "about" or "approximately" another particular value. When such a range is expressed, other exemplary embodiments include the one particular value and/or to the other particular value.

By "comprising" or "containing" or "including" is meant that at least the name compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5).

Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The following patents, applications and publications, as listed below and throughout this document, are hereby incorporated by reference in their entirety herein.

REFERENCES

[1] Lee, W., Lee, B., Yang, X., Jung, H., Bok, I., Kim, C., Kwon, O., and You, H. (2018) A 3D anthropometric sizing analysis system based on North American CAESAR 3D scan data for design of head wearable products. Computers & Industrial Engineering 117, 121-130. doi:10.1016/j.cie.2018.01.023.

[2] D'Agostino, S. (2019) "Voronoi Tessellations and Scutoids Are Everywhere", Scientific American, January, blogs.scientificamerican.com/observations/voronoi-tessellations-and-scutoids-are-everywhere/

[3] Zhuang, Z., & Bradtmiller, B. (2005) A Head-and-Face Anthropometric Survey of U.S. Respirator Users. *J Occup Environ Hyg. November;* 2 (11): 567-76. DOI: 10.1080/15459620500324727. PMID: 16223715.

[4] 3dMD. (2020) Retrieved from 3dmd.com/products/.

[5] Granta. (2020) Chart from CES EduPack, *ANSYS Granta.* 2019.

[6] Ashby. (2008) The CES EduPack Database of Natural and Man-Made Materials, Version 1.0*, Granta Design*, Cambridge, UK, January 2008.

[7] Shore. (2020) "Shore hardness scale," smooth-on.com/page/durometer-shore-hardness-scale/, Last Accessed: Nov. 14, 2020.

[8] Formlabs. (2022a) Elastic 50A, formlabs.com/materials/flexible-elastic/. Last Accessed: Jun. 19, 2022.

[9] Carbon 3D. (2022) SIL 30, carbon3d.com/materials/sil-30, Last Accessed: Jun. 18, 2022.

[10] Dow. (2022) SILASTIC™ 3D 3335 Liquid Silicone Rubber,dow.com/en-us/pdp.silastic-3-d-3335-liquid-silicone-rubber-lsr.4137603z.html?productCatalogFlag=1#overview, Last Accessed: Jun. 18, 2022

[11] Elkem. (2019) Silicones 3D Flyer Industrial, elkem-.com/silicones/brands/amsil/, Last Accessed: Jun. 18, 2022

[12] Institute of Medicine. 2008. Preparing for an Influenza Pandemic: Personal Protective Equipment for Healthcare Workers. Washington, DC, doi.org/10.17226/11980.

[13] Institute of Medicine. 2006. Reusability of Facemasks During an Influenza Pandemic: Facing the Flu. Washington, DC, doi.org/10.17226/11637.

[14] National Academies of Sciences, Engineering, and Medicine. 2019. Reusable Elastomeric Respirators in Health Care: Considerations for Routine and Surge Use. Washington, DC: The National Academies Press. doi.org/10.17226/25275.

[15] Jayaraman, S., and Park, S., Respiratory Protection Device, U.S. Pat. No. 10,646,731, May 2020. Roberge, R., Niezgoda, G., & Benson, S. (2012) Analysis of Forces Generated by N95 Filtering Facepiece Respirator Tethering Devices: A Pilot Study, *Journal of Occupational and Environmental Hygiene,* 9 (8), pp. 527-533.

[17] Zhuang, Z., Bergman, M., Lei, Z., Niezgoda, G. & Shaffer, R. (2017) Recommended test methods and pass/fail criteria for a respirator fit capability test of half-mask air-purifying respirators. *J. Occup. Environ. Hyg.* 14, 473-481. doi.org/10.1080/15459624.2017.1296233.

[18] Yang J, Dai J, Zhuang Z. Simulating the interaction between a respirator and a headform using LS-DYNA. Computer-Aided Design Appl. 2009; 6(4): 539-551.

[19] Protecting facial skin under N95 face masks, National Pressure Injury Advisory Panel, cdn.ymaws.com/npiap.com/resource/resmgr/position_statements/NPIAP_-_Mask_Injury_Infograp.pdf, Last Accessed: Jun. 19, 2020.

[20] Stokowski, L. A. (2020) A Step-by-Step Guide to Preventing PPE-Related Skin Damage. MedScape. Retrieved from medscape.com/viewarticle/929590.

[21] Lam, U-Nee., Siddik, Nur., Yussof, Shah., and Ibrahim, S. (2020) N95 respirator associated pressure ulcer amongst COVID-19 health care workers, Int Wound J. October; 17(5): 1525-1527, doi:10.1111/iwj.13398.

[22] Oot-Giromini B, Bidwell F C, Heller N B, et al. Pressure ulcer prevention versus treatment, comparative product cost study. Decubitus 1989; 2(3): 52-4.

[23] Cai, M., Li., H., Shen, S., Wang, Y, and Yang, Q. (2018) "Customized design and 3D printing of face seal for an N95 filtering facepiece respirator", Journal of Occupational and Environmental Hygiene, 15:3, 226-234, doi.org/10.1080/15459624.2017.1411598

[24] Chopra, J., Abiakam, N., and Kim, H. (2021) The influence of gender and ethnicity on facemasks and respiratory protective equipment fit: a systematic review and meta-analysis. BMJ Global Health 6: e005537. doi: 10.1136/bmjgh-2021-005537.

[25] Zhuang, Z., Groce, D., Ahlers, H. W., Iskander, W., Landsittel, D., Guffey, S., Benson, S., Viscusi, D., and Shaffer, R. E. (2008) Correlation between Respirator Fit and Respirator Fit Test Panel Cells by Respirator Size. *Journal of Occupational and Environmental Hygiene,* 5(10), 617-628. doi.org/10.1080/15459620802293810

[26] Lin, Y. C., & Chen, C. P. (2017) Characterization of small-to-medium head-and-face dimensions for developing respirator fit test panels and evaluating fit of filtering facepiece respirators with different faceseal design. *PLOS ONE,* 12 (11), e0188638. doi.org/10.1371/journal.pone.0188638.

What is claimed includes:

1. An attachment supporting apparatus for a respiratory protective device comprising:

a support member having a contour with a central hub region defining an inner surface configured to contact and maintain engagement against a parietal region of a head of a person, and an outer surface opposite from the inner surface, wherein the support member is connected to the respiratory protective device to maintain a pre-defined position of the respiratory protective device over a facial region of the person; and a plurality of anchorable structures extending outwardly from a circumferential edge of the support member to define a plurality of holes along the circumferential edge of the support member, wherein the plurality of holes are defined to extend through the support member from the outer surface to the inner surface in a direction perpendicular to the contour of the support member.

2. The attachment supporting apparatus of claim 1, wherein the respiratory protective device is a facial covering.

3. The attachment supporting apparatus of claim 1, wherein the plurality of anchorable structures includes two or more anchorable structures extending outwardly from the circumferential edge of the support member.

4. The attachment supporting apparatus of claim 1, wherein the support member defines a plurality of gaps or is formed of a mesh material to provide a lightweight, breathable surface.

5. The attachment supporting apparatus of claim 4, wherein a plurality of struts of the support member define the plurality of gaps, which have a set of pre-defined shapes.

6. The attachment supporting apparatus of claim 5, wherein the set of pre-defined shapes of the plurality of struts and the plurality of gaps defined thereby form a tessellating pattern.

7. The attachment supporting apparatus of claim 4, wherein the plurality of gaps are offset from the circumferential edge by a margin.

8. The attachment supporting apparatus of claim 1, further comprising straps, wherein the straps comprise a marking or calibration scale for customizing and controlling the pressure exerted by the respiratory protective device on the facial region of the person.

9. The attachment supporting apparatus of claim 8, wherein the straps extend from, or are coupled to, two or more anchorable structures of the plurality of anchorable structures, wherein the two or more anchorable structures are selected for customizing and controlling the pressure exerted by the respiratory protective device on the facial region of the person.

10. The attachment supporting apparatus of claim 1, wherein the contour is over, or in proximity to, at least one of:

a vertex region of the head;

an occiput region of the head;

an inion region of the head; or any region therebetween.

11. The attachment supporting apparatus of claim 1, wherein the support member and the contour associated with the support member are customized to a scanned head profile of a back of the head of the person.

12. The attachment supporting apparatus of claim 1, wherein the support member is constructed via additive manufacturing or injection molding using elastomeric materials.

13. The attachment supporting apparatus of claim 1, wherein the support member comprises ethyl-vinyl acetate, silicones, polyurethanes, or neoprene.

14. The attachment supporting apparatus of claim 1, wherein the support member comprises a material compatible with a decontaminating operation comprising UV radiation or cleaning solvents.

15. The attachment supporting apparatus of claim 1, wherein the support member includes a cavity or recess to house electronic components.

16. The attachment supporting apparatus of claim 1, further comprising an electronics module and an active device each coupled to the support member.

17. The attachment supporting apparatus of claim 1, wherein the plurality of anchorable structures are integral to the support member such that the plurality of holes are defined through the support member from the inner surface to the outer surface.

18. A system comprising:

an attachment supporting apparatus for a respiratory protective device comprising:

a support member having a contour with a central hub region defining an inner surface configured to contact and maintain engagement against a parietal region of a head of a person, and an outer surface opposite from the inner surface, wherein the support member is connected to the respiratory protective device to maintain a pre-defined position of the respiratory protective device over a facial region of the person; and a plurality of anchorable structures extending outwardly from a circumferential edge of the support member to define a plurality of holes along the circumferential edge of the support member, wherein the plurality of holes are defined to extend through the support member from the outer surface to the inner surface in a direction perpendicular to the contour of the support member;

the respiratory protective device having a plurality of corresponding anchorable structures; and two or more straps to connect the respiratory protective device to the attachment supporting apparatus, wherein each of the two or more straps is configurable between at least a first length and a second length.

19. A method of fabricating an attachment supporting apparatus for a respiratory-protective-device, the method comprising:

acquiring (i) a set of images or scans of a person or (ii) a scanned head profile of a head of the person;

generating, by a processor, a model of the head of the person based on (i) the set of images or scans of the person or (ii) the scanned head profile of the person;

determining, by the processor, a plurality of anthropometric landmarks, or landmarks derived therefrom, wherein the plurality of anthropometric landmarks, or landmarks derived therefrom, include at least one of a vertex region of the head, an occiput region of the head, an inion region of the head, any region therebetween, or any region proximal thereto; and determining, by the processor, using the determined plurality of anthropometric landmarks, or landmarks derived therefrom, a support member having a contour with a central hub region defining an inner surface configured to contact and maintain engagement against the head of the person, and an outer surface opposite from the inner surface, wherein a plurality of anchorable structures extend outwardly from a circumferential edge of the support member, wherein the support member and the contour thereof extends over at least one of the vertex region of the head, the occiput region of the head, the inion region of the head, any region therebetween, or any region proximal thereto;

wherein the support member and the plurality of anchorable structures thereof is employed in one or more manufacturing operations to manufacture or fabricate the attachment supporting apparatus.

20. A method comprising:

providing an attachment supporting apparatus for a respiratory protective device comprising:

a support member having a contour with a central hub region defining an inner surface configured to contact and maintain engagement against a parietal region of a head of a person, and an outer surface opposite from the inner surface, wherein the support member is connected to the respiratory protective device to maintain a pre-defined position of the respiratory protective device over a facial region of the person; and a plurality of anchorable structures extending outwardly from a circumferential edge of the support member to define a plurality of holes along the circumferential edge of the support member, wherein the plurality of holes are defined to extend through the support member from the outer surface to the inner surface in a direction perpendicular to the contour of the support member;

measuring a head region of the person to obtain a plurality of anatomical facial landmarks; and fitting the attachment supporting apparatus or the contour to the head region of the person such that the central hub region and the inner surface thereof contacts and maintains engagement against a parietal region of the person.

* * * * *